(12) United States Patent
Williams et al.

(10) Patent No.: US 7,390,798 B2
(45) Date of Patent: Jun. 24, 2008

(54) CARBOXAMIDE SPIROLACTAM CGRP RECEPTOR ANTAGONISTS

(75) Inventors: Theresa M. Williams, Harleysville, PA (US); Christopher S. Burgey, Philadelphia, PA (US); Thomas J. Tucker, North Wales, PA (US); Craig A. Stump, Pottstown, PA (US); Ian M. Bell, Harleysville, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 11/660,798

(22) PCT Filed: Feb. 9, 2005

(86) PCT No.: PCT/US2005/032036

§ 371 (c)(1), (2), (4) Date: Feb. 21, 2007

(87) PCT Pub. No.: WO2006/031606

PCT Pub. Date: Mar. 23, 2006

(65) Prior Publication Data

US 2007/0293470 A1 Dec. 20, 2007

Related U.S. Application Data

(60) Provisional application No. 60/609,436, filed on Sep. 13, 2004.

(51) Int. Cl.
- C07D 401/14 (2006.01)
- C07D 471/10 (2006.01)
- A61K 31/553 (2006.01)
- A61K 31/55 (2006.01)
- A61K 31/438 (2006.01)
- A61K 31/4166 (2006.01)
- A61P 25/06 (2006.01)

(52) U.S. Cl. ............... 514/211.05; 514/211.06; 514/211.07; 514/211.09; 514/211.1; 514/211.15; 514/212.07; 514/212.08; 514/214.02; 514/217.03; 514/307; 514/309; 514/311; 514/320; 514/386; 514/387; 514/409; 540/491; 540/523; 540/524; 540/578; 540/593; 546/15; 546/150; 546/176; 546/200; 546/276.7; 548/305.1; 548/311.4; 548/411

(58) Field of Classification Search ............ 514/211.05, 514/211.06, 211.07, 211.09, 211.1, 211.15, 514/212.07, 212.08, 214.02, 217.03, 307, 514/309, 311, 320, 386, 387, 409; 540/491, 540/523, 524, 578, 593; 546/15, 150, 176, 546/200, 276.7; 548/305.1, 311.4, 411
See application file for complete search history.

(56) References Cited

FOREIGN PATENT DOCUMENTS

| WO | WO 2004/082602 | 9/2004 |
|----|----------------|--------|
| WO | WO 2004/087649 | 10/2004 |

*Primary Examiner*—Bruck Kifle
(74) *Attorney, Agent, or Firm*—John C. Todaro; William Krovatin

(57) ABSTRACT

The present invention is directed to compounds of Formula I: I (where variables $A^1$, $A^2$, B, J, K, m, n, $R^4$, $R^{5a}$, $R^{5b}$ and $R^{5c}$ are as defined herein) useful as antagonists of CGRP receptors and useful in the treatment or prevention of diseases in which the CGRP is involved, such as headache, migraine and cluster headache. The invention is also directed to pharmaceutical compositions comprising these compounds and the use of these compounds and compositions in the prevention or treatment of such diseases in which CGRP is involved

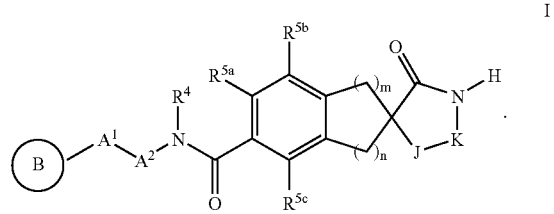

23 Claims, No Drawings

US 7,390,798 B2

CARBOXAMIDE SPIROLACTAM CGRP RECEPTOR ANTAGONISTS

RELATED APPLICATION DATA

This is a National filing under 35 USC 371 of PCT/US2005/032036, filed Sep. 9, 2005, which claims priority from USSN 60/609,436, filed Sep. 13, 2004.

BACKGROUND OF THE INVENTION

CGRP (Calcitonin Gene-Related Peptide) is a naturally occurring 37-amino acid peptide that is generated by tissue-specific alternate processing of calcitonin messenger RNA and is widely distributed in the central and peripheral nervous system. CGRP is localized predominantly in sensory afferent and central neurons and mediates several biological actions, including vasodilation. CGRP is expressed in alpha- and beta-forms that vary by one and three amino acids in the rat and human, respectively. CGRP-alpha and CGRP-beta display similar biological properties. When released from the cell, CGRP initiates its biological responses by binding to specific cell surface receptors that are predominantly coupled to the activation of adenylyl cyclase. CGRP receptors have been identified and pharmacologically evaluated in several tissues and cells, including those of brain, cardiovascular, endothelial, and smooth muscle origin.

Based on pharmacological properties, these receptors are divided into at least two subtypes, denoted $CGRP_1$ and $CGRP_2$. Human □-CGRP-(8-37), a fragment of CGRP that lacks seven N-terminal amino acid residues, is a selective antagonist of $CGRP_1$, whereas the linear analogue of CGRP, diacetoamido methyl cysteine CGRP ([Cys(ACM)2,7] CGRP), is a selective agonist of $CGRP_2$. CGRP is a potent vasodilator that has been implicated in the pathology of cerebrovascular disorders such as migraine and cluster headache. In clinical studies, elevated levels of CGRP in the jugular vein were found to occur during migraine attacks (Goadsby et al., Ann. Neurol., 1990, 28, 183-187). CGRP activates receptors on the smooth muscle of intracranial vessels, leading to increased vasodilation, which is thought to be the major source of headache pain during migraine attacks (Lance, Headache Pathogenesis: Monoamines, Neuropeptides, Purines and Nitric Oxide, Lippincott-Raven Publishers, 1997, 3-9). The middle meningeal artery, the principle artery in the dura mater, is innervated by sensory fibers from the trigeminal ganglion which contain several neuropeptides, including CGRP. Trigeminal ganglion stimulation in the cat resulted in increased levels of CGRP, and in humans, activation of the trigeminal system caused facial flushing and increased levels of CGRP in the external jugular vein (Goadsby et al., Ann. Neurol., 1988, 23, 193-196). Electrical stimulation of the dura mater in rats increased the diameter of the middle meningeal artery, an effect that was blocked by prior administration of CGRP(8-37), a peptide CGRP antagonist (Williamson et al., Cephalalgia, 1997, 17, 525-531). Trigeminal ganglion stimulation increased facial blood flow in the rat, which was inhibited by CGRP(8-37) (Escott et al., Brain Res. 1995, 669, 93-99). Electrical stimulation of the trigeminal ganglion in marmoset produced an increase in facial blood flow that could be blocked by the non-peptide CGRP antagonist BIBN4096BS (Doods et al., Br. J. Pharmacol., 2000, 129, 420-423). Thus the vascular effects of CGRP may be attenuated, prevented or reversed by a CGRP antagonist.

CGRP-mediated vasodilation of rat middle meningeal artery was shown to sensitize neurons of the trigeminal nucleus caudalis (Williamson et al., The CGRP Family: Calcitonin Gene-Related Peptide (CGRP), Amylin, and Adrenomedullin, Landes Bioscience, 2000, 245-247). Similarly, distention of dural blood vessels during migraine headache may sensitize trigeminal neurons. Some of the associated symptoms of migraine, including extra-cranial pain and facial allodynia, may be the result of sensitized trigeminal neurons (Burstein et al., Ann. Neurol. 2000, 47, 614-624). A CGRP antagonist may be beneficial in attenuating, preventing or reversing the effects of neuronal sensitization.

The ability of the compounds of the present invention to act as CGRP antagonists makes them useful pharmacological agents for disorders that involve CGRP in humans and animals, but particularly in humans. Such disorders include migraine and cluster headache (Doods, Curr Opin Inves Drugs, 2001, 2 (9), 1261-1268; Edvinsson et al., Cephalalgia, 1994, 14, 320-327); chronic tension type headache (Ashina et al., Neurology, 2000, 14, 1335-1340); pain (Yu et al., Eur. J. Pharm., 1998, 347, 275-282); chronic pain (Hulsebosch et al., Pain, 2000, 86, 163-175); neurogenic inflammation and inflammatory pain (Holzer, Neurosci., 1988, 24, 739-768; Delay-Goyet et al., Acta Physiol. Scanda. 1992, 146, 537-538; Salmon et al., Nature Neurosci., 2001, 4(4), 357-358); eye pain (May et al. Cephalalgia, 2002, 22, 195-196), tooth pain (Awawdeh et al., int. Endocrin. J., 2002, 35, 30-36), non-insulin dependent diabetes mellitus (Molina et al., Diabetes, 1990, 39, 260-265); vascular disorders; inflammation (Zhang et al., Pain, 2001, 89, 265), arthritis, bronchial hyperreactivity, asthma, (Foster et al., Ann. NY Acad. Sci., 1992, 657, 397-404; Schini et al., Am. J. Physiol., 1994, 267, H2483-H2490; Zheng et al., J. Virol., 1993, 67, 5786-5791); shock, sepsis (Beer et al., Crit. Care Med., 2002, 30 (8), 1794-1798); opiate withdrawal syndrome (Salmon et al., Nature Neurosci., 2001, 4(4), 357-358) morphine tolerance (Menard et al., J. Neurosci., 1996, 16 (7), 2342-2351); hot flashes in men and women (Chen et al., Lancet, 1993, 342, 49; Spetz et al., J. Urology, 2001, 166, 1720-1723); allergic dermatitis (Wallengren, Contact Dermatitis, 2000, 43 (3), 137-143); psoriasis; encephalitis, brain trauma, ischaemia, stroke, epilepsy, and neurodegenerative diseases (Rohrenbeck et al., Neurobiol. of Disease 1999, 6, 15-34); skin diseases (Geppetti and Holzer, Eds., Neurogenic Inflammation, 1996, CRC Press, Boca Raton, Fla.), neurogenic cutaneous redness, skin rosaceousness and erythema; tinnitus (Herzog et al., J. Membrane Biology, 2002, 189(3), 225); inflammatory bowel disease, irritable bowel syndrome, (Hoffman et al. Scandinavian Journal of Gastroenterology, 2002, 37(4) 414-422) and cystitis. Of particular importance is the acute or prophylactic treatment of headache, including migraine and cluster headache. Compelling evidence of the efficacy of CGRP antagonists for the treatment of migraine has been provided by clinical studies using intravenously administered BIBN4096BS. This CGRP antagonist was found to be a safe and effective acute treatment for migraine (Olesen et al., N. Engl. J. Med., 2004, 350(11), 1104-1110).

The present invention relates to compounds that are useful as ligands for CGRP receptors, in particular antagonists for CGRP receptors, processes for their preparation, their use in therapy, pharmaceutical compositions comprising them and methods of therapy using them.

SUMMARY OF THE INVENTION

The present invention is directed to compounds which are antagonists of CGRP receptors and which are useful in the treatment or prevention of diseases in which the CGRP is involved, such as migraine. The invention is also directed to pharmaceutical compositions comprising these compounds and the use of these compounds and compositions in the prevention or treatment of such diseases in which CGRP is involved.

DETAILED DESCRIPTION OF THE INVENTION

The present invention is directed to compounds of the formula I:

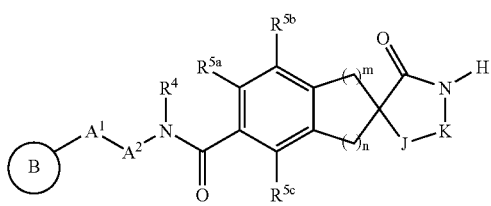

I wherein:

B is a selected from the group consisting of: $C_{3-10}$cycloalkyl, phenyl, naphthyl, tetrahydronaphthyl, indanyl, biphenyl, phenanthryl, anthryl, azepanyl, azetidinyl, benzimidazolyl, benzisoxazolyl, benzofuranyl, benzofurazanyl, benzopyranyl, benzothiopyranyl, benzofuryl, benzothiazolyl, benzothienyl, benzoxazolyl, benzopyrazolyl, benzotriazolyl, chromanyl, cinnolinyl, dibenzofuranyl, dihydrobenzofuryl, dihydrobenzothienyl, dihydrobenzothiopyranyl, dihydrobenzothiopyranyl sulfone, furyl, furanyl, imidazolidinyl, imidazolinyl, imidazolyl, indolinyl, indolyl, isochromanyl, isoindolinyl, isoquinolinyl, isothiazolidinyl, isothiazolyl, morpholinyl, naphthyridinyl, oxazepanyl, oxadiazolyl, 2-oxoazepinyl, 4-oxonaphthyridinyl, 2-oxopiperazinyl, 2-oxopiperidinyl, 2-oxopyrrolidinyl, 2-oxopyridinyl, 2-oxoquinolinyl, 2-oxobenzimidazolyl, piperidinyl, piperazinyl, pyrazinyl, pyrazolidinyl, pyrazolyl, pyridazinyl, pyridinyl, pyridinyl, pyrimidinyl, pyrimidyl, pyrrolidinyl, pyrrolyl, quinazolinyl, quinolinyl, quinoxalinyl, tetrahydrofuranyl, tetrahydrofuryl, tetrahydroimidazopyridinyl, tetrahydroisoquinolinyl, tetrahydroquinolinyl, tetrazolyl, thiamorpholinyl, thiamorpholinyl sulfoxide, thiazepinyl, thiazolyl, thiazolinyl, thiazolidinyl, thienyl, and triazolyl, where B is unsubstituted or substituted with 1-5 substituents each independently selected from $R^1$, $R^2$, $R^{3a}$ and $R^{3b}$, $R^1$, $R^2$, $R^{3a}$ and $R^{3b}$ are independently selected from:
(1) —$C_{1-6}$alkyl, which is unsubstituted or substituted with 1-7 substituents each independently selected from:
  (a) halo,
  (b) hydroxy,
  (c) —O—$C_{1-6}$alkyl,
  (d) —$C_{3-6}$cycloalkyl,
  (e) phenyl or heterocycle, wherein heterocycle is selected from: pyridinyl, pyrimidinyl, pyrazinyl, pyridazinyl, piperidinyl, piperazinyl, pyrrolidinyl, thienyl and morpholinyl,
    which phenyl or heterocycle is unsubstituted or substituted with 1-5 substituents each independently selected from: —$C_{1-6}$alkyl, —O—$C_{1-6}$alkyl, halo, hydroxy, trifluoromethyl and —$OCF_3$,
  (f) —$CO_2R^9$, wherein $R^9$ is selected from: hydrogen, —$C_{1-6}$alkyl which is unsubstituted or substituted with 1-6 fluoro, —$C_{5-6}$cycloalkyl, benzyl and phenyl,
  (g) —$NR^{10}R^{11}$, wherein $R^{10}$ and $R^{11}$ are each independently selected from: hydrogen, —$C_{1-6}$alkyl which is unsubstituted or substituted with 1-6 fluoro, —$C_{5-6}$cycloalkyl, benzyl, phenyl, —$COR^9$ and —$SO_2R^{12}$,
  (h) —$SO_2R^{12}$, wherein $R^{12}$ is selected from: —$C_{1-6}$alkyl which is unsubstituted or substituted with 1-6 fluoro, —$C_{5-6}$cycloalkyl, benzyl and phenyl,
  (i) —$CONR^{10a}R^{11a}$, wherein $R^{10a}$ and $R^{11a}$ are each independently selected from:
    hydrogen, —$C_{1-6}$alkyl which is unsubstituted or substituted with 1-6 fluoro, —$C_{5-6}$cycloalkyl, benzyl and phenyl,
    or $R^{10a}$ and $R^{11a}$ are joined to form a ring selected from azetidinyl, pyrrolidinyl, piperidinyl, piperazinyl and morpholinyl, which ring is unsubstituted or substituted with 1-5 substituents each independently selected from: —$C_{1-6}$alkyl, —O—$C_{1-6}$alkyl, halo, hydroxyl, phenyl and benzyl,
  (j) trifluoromethyl,
  (k) —$OCO_2R^9$,
  (l) —$(NR^{10a})CO_2R^9$,
  (m) —$O(CO)NR^{10a}R^{11a}$, and
  (n) —$(NR^9)(CO)NR^{10a}R^{11a}$,
(2) —$C_{3-6}$cycloalkyl, which is unsubstituted or substituted with 1-7 substituents each independently selected from: halo, hydroxy, —O—$C_{1-6}$alkyl, trifluoromethyl and phenyl, which phenyl is unsubstituted or substituted with 1-5 substituents each independently selected from: —$C_{1-6}$alkyl, —O—$C_{1-6}$alkyl, halo, hydroxy and trifluoromethyl,
(3) phenyl or heterocycle, wherein heterocycle is selected from: pyridinyl, pyrimidinyl, pyrazinyl, thienyl, pyridazinyl, pyrrolidinyl, azetidinyl, thiazolyl, isothiazolyl, oxazolyl, isoxazolyl, imidazolyl, triazolyl, tetrazolyl, azepanyl, benzimidazolyl, benzopyranyl, benzofuryl, benzothiazolyl, benzoxazolyl, chromanyl, furyl, imidazolidinyl, imidazolinyl, indolinyl, indolyl, quinolinyl, isoquinolinyl, tetrahydroquinolinyl, isoindolinyl, tetrahydroisoquinolinyl, 2-oxopiperazinyl, 2-oxopiperidinyl, 2-oxopyrrolidinyl, pyrazolidinyl, pyrazolyl, pyrrolyl, quinazolinyl, tetrahydrofuryl, thiazolinyl, purinyl, naphthyridinyl, quinoxalinyl, quinazolinyl, 1,3-dioxolanyl, oxadiazolyl, piperidinyl and morpholinyl, which phenyl or heterocycle is unsubstituted or substituted with 1-5 substituents each independently selected from:
  (a) —$C_{1-6}$alkyl which is unsubstituted or substituted with 1-6 fluoro,
  (b) halo,
  (c) hydroxy,
  (d) —O—$C_{1-6}$alkyl, which is unsubstituted or substituted with 1-6 fluoro,
  (e) —$C_{3-6}$cycloalkyl,
  (f) phenyl or heterocycle, wherein heterocycle is selected from: pyridinyl, pyrimidinyl, pyrazinyl, thienyl and morpholinyl, which phenyl or heterocycle is unsubstituted or substituted with 1-5 substituents each independently selected from: —$C_{1-6}$alkyl, —O—$C_{1-6}$alkyl, halo, hydroxy and trifluoromethyl,
  (g) —$CO_2R^9$,
  (h) —$NR^{10}R^{11}$,
  (i) —$CONR^{10}R^{11}$,
  (j) —$SO_2R^{12}$, and
  (k) oxo,
(4) halo,
(5) oxo,
(6) hydroxy, (7) —O—$C_{1-6}$alkyl, which is unsubstituted or substituted with 1-5 halo,
(8) —CN,
(9) —$CO_2R^9$,
(10) —$NR^{10}R^{11}$,
(11) —$SO_2R^{12}$,
(12) —$CONR^{10a}R^{11a}$,
(13) —$OCO_2R^9$,
(14) —$(NR^{10a})CO_2R^9$,
(15) —$O(CO)NR^{10a}R^{11a}$,
(16) —$(NR_9)(CO)NR^{10a}R^{11a}$,
(17) —$SO_2NR^{10a}R^{11a}$,
(18) —$SR^{12}$,
(19) —$S(O)R^{12}$,
(20) —$(NR^9)(CO)NR^{10a}R^{11a}$,
(21) —(CO)—$(CO)NR^{10a}R^{11a}$, and
(22) —(CO)—$(CO)OR^9$;

or $R^{3a}$ and $R^{3b}$ and the atom(s) to which they are attached are joined to form a ring selected from cyclobutyl, cyclopentenyl, cyclopentyl, cyclohexenyl, cyclohexyl, phenyl, naphthyl, thienyl, thiazolyl, thiazolinyl, oxazolyl, oxazolinyl, imidazolyl, imidazolinyl, imidazolidinyl, thiadiazolyl, oxadiazolyl, isoxazolyl, pyrazolyl, triazolyl, pyridinyl, pyrimidyl, pyrazinyl, pyridazinyl, triazinyl, pyrrolyl, pyrrolinyl, morpholinyl, azetidinyl, pyrrolidinyl, piperidinyl, tetrahydrofuranyl, tetrahydropyranyl, tetrahydropyridinyl, furanyl, dihydrofuranyl, dihydropyranyl and piperazinyl, which ring is unsubstituted or substituted with 1-5 substituents each independently selected from:
  (a) —$C_{1-6}$alkyl, which is unsubstituted or substituted with 1-3 substituents each independently selected from:
    (i) halo,
    (ii) hydroxy,
    (iii) —O—$C_{1-6}$alkyl, which is unsubstituted or substituted with 1-5 substituents each independently selected from: —O—$C_{1-6}$alkyl, halo, and hydroxy,
    (iv) —$C_{3-6}$cycloalkyl, which is unsubstituted or substituted with 1-5 substituents each independently selected from: —$C_{1-6}$alkyl, —O—$C_{1-6}$alkyl, halo, hydroxy, trifluoromethyl and —$OCF_3$, (v) phenyl or heterocycle, wherein heterocycle is selected from: pyridinyl, pyrimidinyl, pyrazinyl, pyridazinyl, piperidinyl, piperazinyl, pyrrolidinyl, thienyl and morpholinyl, which phenyl or heterocycle is unsubstituted or substituted with 1-5 substituents each independently selected from: —$C_{1-6}$alkyl, —O—$C_{1-6}$alkyl, halo, hydroxy, trifluoromethyl and —$OCF_3$,
    (vi) —$CO_2R^9$,
    (vii) —$NR^{10}R^{11}$,
    (viii) —$SO_2R^{12}$,
    (ix) —$CONR^{10a}R^{11a}$, and
    (x) —$(NR^{10a})CO_2R^9$,
  (b) —$C_{3-6}$cycloalkyl, which is unsubstituted or substituted with 1-5 substituents each independently selected from: halo, hydroxy, —O—$C_{1-6}$alkyl, trifluoromethyl and phenyl, (c) phenyl or heterocycle, wherein heterocycle is selected from: pyridinyl, pyrimidinyl, pyrazinyl, thienyl, pyridazinyl, pyrrolidinyl, azetidinyl, piperidinyl and morpholinyl, which phenyl or heterocycle is unsubstituted or substituted with 1-3 substituents each independently selected from: halo, hydroxy, —$C_{3-6}$cycloalkyl, —O—$C_{1-6}$alkyl which is unsubstituted or substituted with 1-6 fluoro, and —$C_{1-6}$alkyl which is unsubstituted or substituted with 1-6 fluoro,
    (d) halo,
    (e) —$SO_2R^{12}$,
    (f) hydroxy,
    (g) —O—$C_{1-6}$alkyl which is unsubstituted or substituted with 1-5 halo,
    (h) —CN,
    (i) —$COR^{12}$,
    (j) —$NR^{10}R^{11}$,
    (k) —$CONR^{10a}R^{11a}$,
    (l) —$CO_2R^9$,
    (m) —$(NR^{10a})CO_2R^9$,
    (n) —$O(CO)NR^{10a}R^{11a}$,
    (o) —$(NR^9)(CO)NR^{10a}R^{11a}$, and
    (p) oxo;

$A^1$ and $A^2$ are each independently selected from:
(1) a bond,
(2) —$CR^{13}R^{14}$—, wherein $R^{13}$ and $R^{14}$ are independently selected from:
  (a) hydrogen,
  (b) $C_{1-6}$ alkyl, which is unsubstituted or substituted with 1-5 substituents each independently selected from: halo, hydroxy, —$NR^{10}R^{11}$, —$CONR^{10a}R^{11a}$ and —$CO_2R^9$,
  (c) phenyl, which is unsubstituted or substituted with 1-3 substituents each independently selected from: $C_{1-4}$alkyl, hydroxyl and halo,
  (d) —$CONR^{10}$—($C_{1-6}$alkyl)—$NR^{15}R^{16}$, wherein $R^{15}$ and $R^{16}$ are each independently selected from: hydrogen, —$C_{1-6}$alkyl, —$COR^9$ and —$CO_2R^9$,
  (e) —$CO_2R^9$,
  (f) —$CONR^{10a}R^{11a}$, and
  (g) hydroxy, and
(3) —$CH_2CR^{13}R^{14}$—,
wherein one of $A^1$ and $A^2$ is optionally absent;
J is selected from: =$C(R^{6a})$—, —$CR^{13}R^{14}$— and —C(=O)—;
K is selected from: =$C(R^{6b})$—, —$CR^{13}R^{14}$—, —C(=O)—, —$SO_2$—, =N— and —$N(R^{6b})$—;
$R^4$ is selected from: hydrogen, $C_{1-6}$ alkyl which is unsubstituted or substituted with 1-6 fluoro, $C_{5-6}$ cycloalkyl, benzyl and phenyl,
or $R^4$ is joined to B to form a ring selected from piperidinyl, pyrrolidinyl, piperazinyl, azetidinyl, azepinyl and morpholinyl, which ring is unsubstituted or substituted with 1-5 substituents each independently selected from: —$C_{1-6}$ alkyl, —O—$C_{1-6}$alkyl, halo, hydroxy, phenyl and benzyl;
$R^{5a}$, $R^{5b}$ and $R^{5c}$ are each independently selected from: hydrogen, $C_{1-6}$ alkyl, —O—$C_{1-6}$alkyl, —$OCF_3$, trifluoromethyl, halo, hydroxy and —CN;
$R^{6a}$ and $R^{6b}$ are each independently selected from:
(1) hydrogen;
(2) —$C_{1-4}$alkyl, which is unsubstituted or substituted with 1-5 substituents each independently selected from:
  (a) halo,
  (b) —O—$C_{1-6}$alkyl,
  (c) —$C_{3-6}$cycloalkyl,
  (d) phenyl or heterocycle, wherein heterocycle is selected from: imidazolyl, oxazolyl, pyridinyl, pyrimidinyl, pyrazinyl, pyridazinyl, piperidinyl, piperazinyl, pyrrolidinyl, thiazolyl, thienyl, triazolyl, or morpholinyl, which phenyl or heterocycle is unsubstituted or substituted with 1-3 substituents each independently selected from: —$C_{1-6}$alkyl, —O—$C_{1-16}$alkyl, halo, hydroxy, trifluoromethyl and —$OCF_3$,
(4) phenyl or heterocycle, wherein heterocycle is selected from: pyridinyl, pyrimidinyl, pyrazinyl, thienyl, pyrrolidinyl, azetidinyl, thiazolyl, oxazolyl, imidazolyl, triazolyl, tetrahydrofuryl, piperidinyl, and morpholinyl, which phenyl or heterocycle is unsubstituted or substituted with 1-3 substituents each independently selected from: —$C_{1-4}$alkyl which is unsubstituted or substituted with 1-5 fluoro, halo, hydroxy, —O—$C_{1-4}$alkyl which is unsubstituted or substituted with 1-5 fluoro, —$C_{3-6}$cycloalkyl and phenyl,
(5) halo,
(6) hydroxy,
(7) —O—$C_{1-6}$alkyl, which is unsubstituted or substituted with 1-5 halo,
(8) —CN,
(9) —$CO_2R^9$,
(10) —$NR^{10}R^{11}$, and
(11) —$CONR^{10a}R^{11a}$,
or $R^{6a}$ and $R^{6b}$ and the atom(s) to which they are attached are joined to form a ring selected from cyclopentenyl, cyclohexenyl, phenyl, pyridinyl, pyrimidinyl, pyrazinyl, pyridazinyl, furanyl, dihydrofuranyl, dihydropyranyl, thiazolyl, isothiazolyl, oxazolyl, isoxazolyl, imidazolyl, triazolyl, thienyl, dihydrothienyl and dihydrothiopyranyl, which ring is unsubstituted or substituted with 1-5 substituents each independently selected from:
(a) —$C_{1-6}$alkyl, which is unsubstituted or substituted with 1-3 substituents each independently selected from:
(i) halo,
(ii) hydroxy,
(iii) —O—$C_{1-6}$alkyl,
(iv) —$C_{3-6}$cycloalkyl,
(v) phenyl or heterocycle, wherein heterocycle is selected from: pyridinyl, pyrimidinyl, pyrazinyl, pyridazinyl, piperidinyl, piperazinyl, pyrrolidinyl, thienyl, or morpholinyl, which is unsubstituted or substituted with 1-5 substituents where the substituents are each independently selected from: —$C_{1-6}$alkyl, —O—$C_{1-6}$alkyl, halo, hydroxy, trifluoromethyl and —$OCF_3$,
(vi) —$CO_2R^9$,
(vii) —$NR^{10}R^{11}$,
(viii) —$SO_2R^{12}$,
(ix) —$CONR^{10a}R^{11a}$, and
(x) —$(NR^{10a})CO_2R^9$,
(b) phenyl or heterocycle, wherein heterocycle is selected from: pyridinyl, pyrimidinyl, pyrazinyl, thienyl, pyridazinyl, pyrrolidinyl, azetidinyl, piperidinyl and morpholinyl, which phenyl or heterocycle is unsubstituted or substituted with 1-3 substituents each independently selected from: —$C_{1-6}$alkyl, which is unsubstituted or substituted with 1-6 fluoro, —O—$C_{1-6}$alkyl, which is unsubstituted or substituted with 1-6 fluoro, halo, hydroxy, and —$C_{3-6}$cycloalkyl,
(c) halo,
(d) —$SO_2R^{12}$,
(e) hydroxy,
(f) —O—$C_{1-6}$alkyl, which is unsubstituted or substituted with 1-5 halo,
(g) —CN,
(h) —$COR^{12}$,
(i) —$NR^{10}R^{11}$,
(j) —$CONR^{10a}R^{11a}$,
(k) —$CO_2R^9$,
(l) —$(NR^{10a})CO_2R^9$,
(m) —$O(CO)NR^{10a}R^{11a}$,
(n) —$(NR^9)(CO)NR^{10a}R^{11a}$, and
(o) oxo;

m is 1 or 2;

n is 1 or 2;

and pharmaceutically acceptable salts thereof and individual enantiomers and diastereomers thereof.

An embodiment of the present invention includes compounds of the formula Ia:

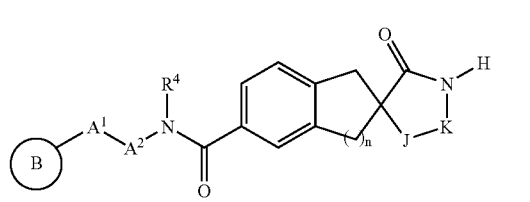

Ia wherein B, $A^1$, $A^2$, $R^4$, J, K, and n are defined herein;

and pharmaceutically acceptable salts thereof and individual enantiomers and diastereomers thereof.

Another embodiment of the present invention includes compounds of the formula Ib:

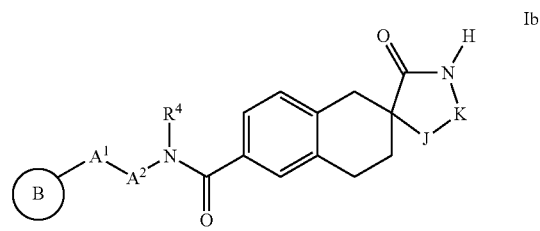

Ib wherein B, $A^1$, $A^2$, $R^4$, J, and K are defined herein;

and pharmaceutically acceptable salts thereof and individual enantiomers and diastereomers thereof.

Another embodiment of the present invention includes compounds of the formula Ic:

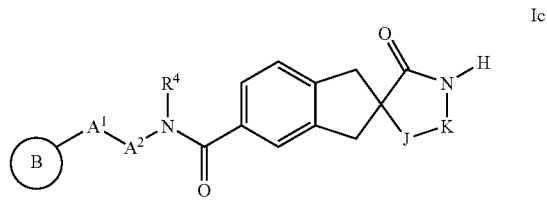

Ic wherein B, $A^1$, $A^2$, $R^4$, J, and K are defined herein;

and pharmaceutically acceptable salts thereof and individual enantiomers and diastereomers thereof.

Another embodiment of the present invention includes compounds of the formula Id:

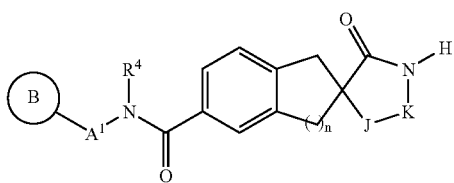

wherein B, A¹, R⁴, J, K, and n are defined herein;

and pharmaceutically acceptable salts thereof and individual enantiomers and diastereomers thereof.

Another embodiment of the present invention includes compounds of the formula Ie:

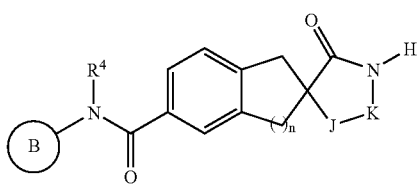

wherein B, R⁴, J, K, and n are defined herein;

and pharmaceutically acceptable salts thereof and individual enantiomers and diastereomers thereof.

Another embodiment of the present invention includes compounds of the formula If:

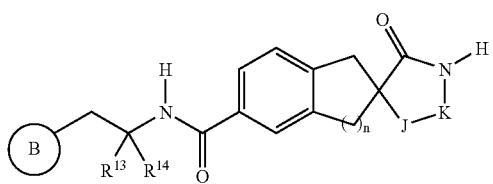

wherein B, J, K, $R^{13}$, $R^{14}$, and n are defined herein;

and pharmaceutically acceptable salts thereof and individual enantiomers and diastereomers thereof.

Another embodiment of the present invention includes compounds of the formula Ig:

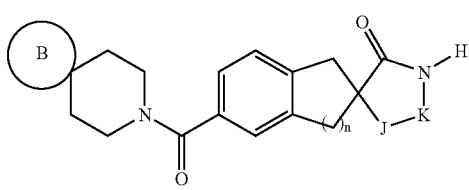

wherein B, J, K, and n are defined herein;

and pharmaceutically acceptable salts thereof and individual enantiomers and diastereomers thereof.

In an embodiment of the present invention B is selected from the group consisting of: $C_{3-10}$cycloalkyl, phenyl, naphthyl, tetrahydronaphthyl, indanyl, biphenyl, azepanyl, benzimidazolyl, imidazolyl, imidazolinyl, imidazolidinyl, indolinyl, indolyl, isoquinolinyl, morpholinyl, naphthyridinyl, oxazepanyl, 2-oxoazepanyl, 2-oxooxazepanyl, 2-oxopyrrolidinyl, 2-oxopyridinyl, piperazinyl, piperidinyl, pyrazinyl, pyridinyl, pyrimidinyl, pyrrolidinyl, pyrrolyl, quinazolinyl, quinolinyl, quinoxalinyl, tetrahydrofuranyl, tetrahydroisoquinolinyl, tetrahydroquinolinyl, thiazolyl, and thiazolinyl, where B is unsubstituted or substituted with 1-5 substituents each independently selected from $R^1$, $R^2$, $R^{3a}$ and $R^{3b}$; wherein $R^1$, $R^2$, $R^{3a}$ and $R^{3b}$ are as defined herein.

In an embodiment of the present invention B is selected from the group consisting of: phenyl, naphthyl, azepanyl, benzimidazolyl, imidazolidinyl, indolinyl, indolyl, isoquinolinyl, oxazepanyl, 2-oxoazepanyl, 2-oxooxazepanyl, 2-oxopyrrolidinyl, 2-oxopyridinyl, piperidinyl, pyridinyl, pyrrolidinyl, pyrrolyl, quinolinyl, tetrahydroisoquinolinyl, tetrahydroquinolinyl, thiazolyl, and thiazolinyl, where B is unsubstituted or substituted with 1-5 substituents each independently selected from $R^1$, $R^2$, $R^{3a}$ and $R^{3b}$; wherein $R^1$, $R^2$, $R^{3a}$ and $R^{3b}$ are defined herein.

In an embodiment of the present invention B is phenyl.
In an embodiment of the present invention B is naphthyl.
In an embodiment of the present invention B is benzimidazolyl.
In an embodiment of the present invention B is thiazolinyl.
In an embodiment of the present invention B is pyridinyl.
In an embodiment of the present invention B is quinolinyl.
In an embodiment of the present invention B is isoquinolinyl.
In an embodiment of the present invention B is pyrrolidinyl.
In an embodiment of the present invention B is indolinyl.
In an embodiment of the present invention B is indolyl.
In an embodiment of the present invention B is azepanyl.
In an embodiment of the present invention B is oxazepanyl.
In an embodiment of the present invention B is imidazolidinyl.
In an embodiment of the present invention B is piperidinyl.
In an embodiment of the present invention B is tetrahydroquinolinyl.
In an embodiment of the present invention B is tetrahydroisoquinolinyl.

In an embodiment of the present invention $R^1$, $R^2$, $R^{3a}$ and $R^{3b}$ are independently selected from:

(1) —$C_{1-6}$alkyl, which is unsubstituted or substituted with 1-5 substituents each independently selected from:
  (a) halo,
  (b) hydroxy,
  (c) —O—$C_{1-6}$alkyl,
  (d) —$C_{3-6}$cycloalkyl,
  (e) phenyl or heterocycle, wherein heterocycle is selected from: pyridinyl, piperidinyl, piperazinyl, pyrrolidinyl, and morpholinyl,
    which phenyl or heterocycle is unsubstituted or substituted with 1-3 substituents each independently selected from: —$C_{1-6}$alkyl, —O—$C_{1-6}$alkyl, halo, hydroxy, trifluoromethyl and —$OCF_3$,
  (f) —$NR^{10}R^{11}$, wherein $R^{10}$ and $R^{11}$ are defined herein, and
  (g) —$CONR^{10a}R^{11a}$, wherein $R^{10a}$ and $R^{11a}$ are defined herein, (2) —$C_{3-6}$cycloalkyl, which is unsubstituted or substituted with 1-5 substituents each independently selected from: halo, hydroxy, —O—$C_{1-6}$alkyl, trifluoromethyl and phenyl, (3) phenyl or heterocycle, wherein heterocycle is selected from: pyridinyl, pyrimidinyl, pyrazinyl, thienyl, pyrrolidinyl, oxazolyl, imidazolyl, triazolyl, tetrazolyl, imidazolidinyl, imidazolinyl, indolinyl, indolyl, quinolinyl, isoquinolinyl, tetrahydroquinolinyl, isoindolinyl, tetrahydroisoquinolinyl, 2-oxopiperazinyl, 2-oxopiperidinyl, 2-oxopyrrolidinyl, tetrahydrofuryl, 1,3-dioxolanyl, oxadiazolyl, piperidinyl and morpholinyl, which phenyl or heterocycle is unsubstituted or substituted with 1-3 substituents each independently selected from:
   (a) —$C_{1-6}$alkyl which is unsubstituted or substituted with 1-6 fluoro,
   (b) halo,
   (c) hydroxy,
   (d) —O—$C_{1-6}$alkyl, which is unsubstituted or substituted with 1-6 fluoro,
   (e) —$C_{3-6}$cycloalkyl,
   (f) phenyl, which is unsubstituted or substituted with 1-3 substituents each independently selected from: —$C_{1-6}$alkyl, —O—$C_{1-6}$alkyl, halo, hydroxy and trifluoromethyl,
   (g) —$NR^{10}R^{11}$, wherein $R^{10}$ and $R^{11}$ are defined herein, and
   (h) oxo,
(4) halo,
(5) oxo,
(6) hydroxy,
(7) —O—$C_{1-16}$alkyl, which is unsubstituted or substituted with 1-5 halo,
(8) —CN,
(9) —$CO_2R^9$, wherein $R^9$ is defined herein,
(10) —$NR^{10}R^{11}$, wherein $R^{10}$ and $R^{11}$ are defined herein,
(11) —$SO_2R^{12}$, wherein $R^{12}$ is defined herein,
(12) —$CONR^{10a}R^{11a}$, wherein $R^{10a}$ and $R^{11a}$ are defined herein, and
(13) —$SO_2NR^{10a}R^{11a}$, wherein $R^{10a}$ and $R^{11a}$ are defined herein.

In an embodiment of the present invention $R^1$, $R^2$, $R^{3a}$ and $R^{3b}$ are independently selected from:
   (1) —$C_{1-6}$alkyl, which is unsubstituted or substituted with 1-5 substituents each independently selected from: halo, hydroxy, —$C_{3-6}$cycloalkyl and phenyl, which phenyl is unsubstituted or substituted with 1-3 substituents each independently selected from: —$C_{1-6}$alkyl, halo and trifluoromethyl,
   (2) phenyl or heterocycle, wherein heterocycle is selected from: pyridinyl, pyrrolidinyl, piperidinyl, piperazinyl, imidazolinyl, imidazolidinyl and morpholinyl, which phenyl or heterocycle is unsubstituted or substituted with 1-3 substituents each independently selected from: —$C_{1-6}$alkyl which is unsubstituted or substituted with 1-6 fluoro, halo and oxo,
   (3) halo,
   (4) oxo,
   (5) hydroxy,
   (6) —O—$C_{1-6}$alkyl, which is unsubstituted or substituted with 1-5 halo,
   (7) —CN,
   (8) —$SO_2R^{12}$, wherein $R^{12}$ is defined herein, and
   (9) —$SO_2NR^{10a}R^{11a}$, wherein $R^{10a}$ and $R^{11a}$ are defined herein or $R^{3a}$ and $R^{3b}$ and the atom(s) to which they are attached are joined to form a ring selected from phenyl, thiazolinyl, triazoyl, imidazolyl, imidazolinyl, pyridinyl, morpholinyl, pyrrolidinyl, piperidinyl, and tetrahydrofuranyl, which ring is unsubstituted or substituted with 1-5 substituents each independently selected from:
   (a) —$C_{1-6}$alkyl, which is unsubstituted or substituted with 1-3 substituents each independently selected from:
      (i) halo,
      (ii) hydroxy,
      (iii) —O—$C_{1-6}$alkyl, which is unsubstituted or substituted with 1-5 substituents each independently selected from: —O—$C_{1-6}$alkyl, halo, and hydroxy,
      (iv) —$C_{3-6}$cycloalkyl, and
   (b) —$C_{3-6}$cycloalkyl, which is unsubstituted or substituted with 1-3 substituents each independently selected from: halo, hydroxy, —O—$C_{1-6}$alkyl, trifluoromethyl and phenyl,
   (c) phenyl or heterocycle, wherein heterocycle is selected from: pyridinyl, pyrrolidinyl, piperidinyl and morpholinyl, which phenyl or heterocycle is unsubstituted or substituted with 1-3 substituents each independently selected from: halo, hydroxy, —$C_{3-6}$cycloalkyl, —O—$C_{1-6}$alkyl, and —$C_{1-6}$alkyl,
   (d) halo,
   (f) hydroxy,
   (g) —O—$C_{1-6}$alkyl which is unsubstituted or substituted with 1-5 halo,
   (i) —$COR^{12}$, wherein $R^{12}$ is defined herein,
   (j) —$NR^{10}R^{11}$, wherein $R^{10}$ and $R^{11}$ are defined herein,
   (k) —$CONR^{10a}R^{11a}$, wherein $R^{10a}$ and $R^{11a}$ are defined herein, and
   (p) oxo;

In an embodiment of the present invention $A^1$ is —$CH_2$— or a bond.

In an embodiment of the present invention $A^2$ is —$CH_2$— or a bond, or $A^2$ is —$CHR^{13}$— wherein $R^{13}$ is defined herein.

In an embodiment of the present invention J is =$C(R^{6a})$— or —$CH_2$—, wherein $R^{6a}$ is defined herein.

In an embodiment of the present invention J is —$CH_2$—.

In an embodiment of the present invention J is =$C(R^{6a})$—, wherein $R^{6a}$ is defined herein.

In an embodiment of the present invention K is selected from:

=$C(R^{6b})$—, —$CH_2$— and —$C(=O)$—, wherein $R^{6b}$ is defined herein.

In an embodiment of the present invention K is —$CH_2$—.

In an embodiment of the present invention K is =$C(R^{6b})$—, wherein $R^{6b}$ is defined herein.

In an embodiment of the present invention $R^4$ is hydrogen or —$C_{1-6}$alkyl which is unsubstituted or substituted with fluoro.

In an embodiment of the present invention $R^4$ is joined to B to form a piperidinyl ring.

In an embodiment of the present invention $R^{5a}$, $R^{5b}$ and $R^{5c}$ are each independently selected from hydrogen, $C_{1-6}$alkyl and halo.

In an embodiment of the present invention $R^{6a}$ and $R^{6b}$ are each independently selected from:
   (1) hydrogen;
   (2) —$C_{1-4}$alkyl, which is unsubstituted or substituted with 1-3 substituents where the substituents are each independently selected from: halo, —O—$C_{1-6}$alkyl, —$C_{3-6}$cycloalkyl, and phenyl,
   (3) phenyl or heterocycle, wherein heterocycle is selected from: pyridinyl, pyrimidinyl, pyrazinyl, thiazolyl, oxazolyl, tetrahydrofuryl, piperidinyl, and morpholinyl, which phenyl or heterocycle is unsubstituted or substituted with 1-3 substituents each independently selected from: halo, hydroxy, —$C_{1-4}$alkyl which is unsubstituted or substituted with 1-3 fluoro, and —O—$C_{1-4}$alkyl which is unsubstituted or substituted with 1-3 fluoro,
(4) halo,
(5) —$NR^{10}R^{11}$,
(6) hydroxy,
(7) —O—$C_{1-4}$alkyl, which is unsubstituted or substituted with 1-3 halo.

In an embodiment of the present invention $R^{6a}$ and $R^{6b}$ are independently selected from:
(1) hydrogen;
(2) —$C_{1-4}$alkyl, which is unsubstituted or substituted with 1-3 fluoro, and
(3) phenyl or heterocycle, wherein heterocycle is selected from: pyridinyl, pyrimidinyl, pyrazinyl, thiazolyl, oxazolyl, tetrahydrofuryl, piperidinyl, and morpholinyl.

In an embodiment of the present invention $R^{6a}$ and $R^{6b}$ and the atom(s) to which they are attached may be joined together to form a ring selected from phenyl, pyridinyl, pyrimidinyl, pyrazinyl, pyridazinyl, thiazolyl, oxazolyl, imidazolyl, thienyl, which ring is unsubstituted or substituted with 1-3 substituents each independently selected from:
(a) —$C_{1-4}$alkyl, which is unsubstituted or substituted with 1-3 substituents each independently selected from: halo, —O—$C_{1-6}$alkyl, —$CO_2R^9$, —$NR^{10}R^{11}$, $CONR^{10a}R^{11a}$,
(b) phenyl or heterocycle, wherein heterocycle is selected from: pyridinyl, pyrimidinyl, pyrazinyl, pyrrolidinyl, azetidinyl, piperidinyl and morpholinyl, which phenyl or heterocycle is unsubstituted or substituted with 1-3 substituents each independently selected from: halo, hydroxyl, —$C_{1-4}$alkyl which is unsubstituted or substituted with 1-5 fluoro, and —O—$C_{1-4}$alkyl which is unsubstituted or substituted with 1-3 fluoro,
(c) halo,
(d) hydroxy,
(e) —O—$C_{1-6}$alkyl which is unsubstituted or substituted with 1-5 halo,
(f) —CN,
(g) —$NR^{10}R^{11}$,
(h) —$CONR^{10a}R^{11a}$, and
(i) oxo.

In an embodiment of the present invention $R^{6a}$ and $R^{6b}$ and the atom(s) to which they are attached are joined to form a ring selected from phenyl, pyridinyl, and pyrimidinyl, which ring is unsubstituted or substituted with 1-3 substituents each independently selected from: —$C_{1-4}$alkyl which is unsubstituted or substituted with 1-3 fluoro, halo, hydroxy and —O—$C_{1-4}$alkyl.

In an embodiment of the present invention $R^{6a}$ and $R^{6b}$ and the atom(s) to which they are attached are joined to form a ring selected from pyridinyl, and pyrimidinyl.

In an embodiment of the present invention $R^{13}$ and $R^{14}$ are independently selected from:
(a) hydrogen,
(b) phenyl,
(c) —$CONR^{10}$—($C_{1-6}$alkyl)-$NR^{15}R^{16}$, wherein $R^{15}$ and $R^{16}$ are independently selected from: hydrogen, —$C_{1-6}$alkyl and —$CO_2R^9$, and
(d) —$CO_2R^9$.

In an embodiment of the present invention m is 1.
In an embodiment of the present invention n is 1.
In an embodiment of the present invention n is 2.

It is to be understood that where one or more of the above recited structures or substructures recite multiple substituents having the same designation each such variable may be the same or different from each similarly designated variable. The invention is not limited to structures and substructures wherein each instance of a particular variable must be the same for a given structure. The same is true with respect to any variable appearing multiple times in a structure or substructure.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

Some of the compounds described herein contain olefinic double bonds, and unless specified otherwise, are meant to include both E and Z geometric isomers.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

As will be appreciated by those of skill in the art, not all of the $R^{10a}$ and $R^{11a}$ substituents are capable of forming a ring structure. Moreover, even those substituents capable of ring formation may or may not form a ring structure.

Also as appreciated by those of skill in the art, halo or halogen as used herein are intended to include chloro, fluoro, bromo and iodo.

As used herein, "alkyl" is intended to mean linear, branched and cyclic structures having no double or triple bonds. Thus $C_{1-6}$alkyl is defined to identify the group as having 1, 2, 3, 4, 5 or 6 carbons in a linear or branched arrangement, such that $C_{1-6}$alkyl specifically includes methyl, ethyl, n-propyl, iso-propyl, n-butyl, iso-butyl, tert-butyl, pentyl and hexyl. "Cycloalkyl" is an alkyl, part or all of which forms a ring of three or more atoms. $C_0$ or $C_0$alkyl is defined to identify the presence of a direct covalent bond.

As used herein, "aryl" is intended to mean any stable monocyclic or bicyclic carbon ring of up to 7 members in each ring, wherein at least one ring is aromatic. Examples of such aryl elements include phenyl, napthyl, tetrahydronapthyl, indanyl, or biphenyl.

The term "heterocycle" or "heterocyclic", as used herein except where noted, represents a stable 5- to 7-membered monocyclic- or stable 8- to 11-membered bicyclic heterocyclic ring system which is either saturated or unsaturated, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic groups include, but are not limited to, azetidine, chroman, dihydrofuran, dihydropyran, dioxane, dioxolane, hexahydroazepine, imidazolidine, imidazolidinone, imidazoline, imidazolinone, indoline, isochroman, isoindoline, isothiazoline, isothiazolidine, isoxazoline, isoxazolidine, morpholine, morpholinone, oxazoline, oxazolidine, oxazolidinone, oxetane, 2-oxohexahydroazepin, 2-oxopiperazine, 2-oxopiperidine, 2-oxopyrrolidine, piperazine, piperidine, pyran, pyrazolidine, pyrazoline, pyrrolidine, pyrroline, quinuclidine, tetrahydrofuran, tetrahydropyran, thiamorpholine, thiazoline, thiazolidine, thiomorpholine and N-oxides thereof.

The term "heteroaryl", as used herein except where noted, represents a stable 4- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, benzimidazole, benzisothiazole, benzisoxazole, benzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyran, pyrazine, pyrazole, pyridazine, pyridine, pyrimidine, pyrrole, quinazoline, quinoline, quinoxaline, tetrazole, thiadiazole, thiazole, thiophene, triazine, triazole, and N-oxides thereof.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The terms "bond" and "absent" are in certain instances herein used interchangeably to refer to an atom (or chemical moiety) which is not present in a particular embodiment of the invention. In such embodiments, the atoms adjacent the "bond" or "absent" atom are simply bonded to one another. For example, in certain embodiments of the invention described and claimed herein, where $A^2$ is described as "absent". In such a molecule, it is understood that $A^1$ is bonded directly to the —C(=O) moiety, resulting in the sub-structure $B^4$-$A^1$-C(=O). The absence of a specific atom or moiety, particularly an atom or moiety which serves to link or connect other atoms or moieties, does not imply that such other atoms or moieties are not linked.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which is selected from the group consisting of the compounds disclosed in the following Examples and pharmaceutically acceptable salts thereof and individual diastereomers thereof.

The subject compounds are useful in a method of antagonism of CGRP receptors in a patient such as a mammal in need of such antagonism comprising the administration of an effective amount of the compound. The present invention is directed to the use of the compounds disclosed herein as antagonists of CGRP receptors. In addition to primates, especially humans, a variety of other mammals can be treated according to the method of the present invention.

Another embodiment of the present invention is directed to a method for the treatment, control, amelioration, or reduction of risk of a disease or disorder in which the CGRP receptor is involved in a patient that comprises administering to the patient a therapeutically effective amount of a compound that is an antagonist of CGRP receptors.

The present invention is further directed to a method for the manufacture of a medicament for antagonism of CGRP receptors activity in humans and animals comprising combining a compound of the present invention with a pharmaceutical carrier or diluent.

The subject treated in the present methods is generally a mammal, for example a human being, male or female, in whom antagonism of CGRP receptor activity is desired. The term "therapeutically effective amount" means the amount of the subject compound that will elicit the biological or medical response of a tissue, system, animal or human that is being sought by the researcher, veterinarian, medical doctor or other clinician. As used herein, the term "treatment" refers both to the treatment and to the prevention or prophylactic therapy of the mentioned conditions, particularly in a patient who is predisposed to such disease or disorder.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as antagonists of CGRP receptor activity may be demonstrated by methodology known in the art. Inhibition of the binding of $^{125}$I-CGRP to receptors and functional antagonism of CGRP receptors were determined as follows:

NATIVE RECEPTOR BINDING ASSAY: The binding of $^{125}$I-CGRP to receptors in SK-N-MC cell membranes was carried out essentially as described (Edvinsson et al. (2001) *Eur. J. Pharmacol.* 415, 39-44). Briefly, membranes (25 μg) were incubated in 1 ml of binding buffer [10 mM HEPES, pH 7.4, 5 mM MgCl$_2$ and 0.2% bovine serum albumin (BSA)] containing 10 pM $^{125}$I-CGRP and antagonist. After incubation at room temperature for 3 h, the assay was terminated by filtration through GFB glass fibre filter plates (Millipore) that had been blocked with 0.5% polyethyleneimine for 3 h. The filters were washed three times with ice-cold assay buffer, then the plates were air dried. Scintillation fluid (50 μl) was added and the radioactivity was counted on a Topcount (Packard Instrument). Data analysis was carried out by using Prism and the $K_i$ was determined by using the Cheng-Prusoff equation (Cheng & Prusoff (1973) *Biochem. Pharmacol.* 22, 3099-3108).

NATIVE RECEPTOR FUNCTIONAL ASSAY: SK-N-MC cells were grown in minimal essential medium (MEM) supplemented with 10% fetal bovine serum, 2 mM L-glutamine, 0.1 mM non-essential amino acids, 1 mM sodium pyruvate, 100 units/ml penicillin and 100 μg/ml streptomycin at 37° C., 95% humidity, and 5% CO$_2$. For cAMP assays, cells were plated at 5×10$^5$ cells/well in 96-well poly-D-lysine-coated plates (Becton-Dickinson) and cultured for ~18 h before assay. Cells were washed with phosphate-buffered saline (PBS, Sigma) then pre-incubated with 300 μM isobutylmethylxanthine in serum-free MEM for 30 min at 37° C. Antagonist was added and the cells were incubated for 10 min before the addition of CGRP. The incubation was continued for another 15 min, then the cells were washed with PBS and processed for cAMP determination according to the manufacturer's recommended protocol. Maximal stimulation over basal was defined by using 100 nM CGRP. Dose-response curves were generated by using Prism. Dose-ratios (DR) were calculated and used to construct full Schild plots (Arunlakshana & Schild (1959) *Br. J. Pharmacol.* 14, 48-58).

RECOMBINANT RECEPTOR: Human CRLR (Genbank accession number L76380) was subcloned into the expression vector pIREShyg2 (BD Biosciences Clontech) as a 5'NheI and 3' PmeI fragment. Human RAMP1 (Genbank accession number AJ001014) was subcloned into the expression vector pIRESpuro2 (BD Biosciences Clontech) as a 5'NheI and 3'NotI fragment. 293 cells (human embryonic kidney cells; ATCC #CRL-1573) were cultured in DMEM with 4.5 g/L glucose, 1 mM sodium pyruvate and 2 mM glutamine supplemented with 10% fetal bovine serum (FBS), 100 units/mL penicillin and 100 ug/ml streptomycin, and maintained at 37° C. and 95% humidity. Cells were subcultured by treatment with 0.25% trypsin with 0.1% EDTA in HBSS. Stable cell line generation was accomplished by co-transfecting 10 ug of DNA with 30 ug Lipofectamine 2000 (Invitrogen) in 75 cm$^2$ flasks. CRLR and RAMP1 expression constructs were co-transfected in equal amounts. Twenty-four hours after transfection the cells were diluted and selective medium (growth medium+300 ug/ml hygromycin and 1 ug/ml puromycin) was added the following day. A clonal cell line was generated by single cell deposition utilizing a FACS Vantage SE (Becton Dickinson). Growth medium was adjusted to 150 ug/ml hygromycin and 0.5 ug/ml puromycin for cell propagation.

RECOMBINANT RECEPTOR BINDING ASSAY: Cells expressing recombinant human CRLR/RAMP1 were washed with PBS and harvested in harvest buffer containing 50 mM HEPES, 1 mM EDTA and Complete protease inhibitors (Roche). The cell suspension was disrupted with a laboratory homogenizer and centrifuged at 48,000 g to isolate membranes. The pellets were resuspended in harvest buffer plus 250 mM sucrose and stored at −70° C. For binding assays, 10 ug of membranes were incubated in 1 ml binding buffer (10 mM HEPES, pH 7.4, 5 mM MgCl$_2$, and 0.2% BSA) for 3 hours at room temperature containing 10 pM $^{125}$I-hCGRP (Amersham Biosciences) and antagonist. The assay was terminated by filtration through 96-well GFB glass fiber filter plates (Millipore) that had been blocked with 0.05% polyethyleneimine. The filters were washed 3 times with ice-cold assay buffer (10 mM HEPES, pH 7.4). Scintillation fluid was added and the plates were counted on a Topcount (Packard). Non-specific binding was determined and the data analysis was carried out with the apparent dissociation constant ($K_i$) determined by using a non-linear least squares fitting the bound CPM data to the equation below:

$$Y_{obsd} = \frac{Y_{min} + (Y_{max} - Y_{min})(100 - \% \, I_{max}/100)}{1 + ([Drug]/K_i(1 + [Radiolabel]/K_d)^{nH}}$$

$$(Y_{max} - Y_{min})(\% \, I_{max} - \%_{I_{min}}/100) +$$

Where Y is observed CPM bound, $Y_{max}$ is total bound counts, Y min is non specific bound counts, (Y max~Y min) is specific bound counts, % I max is the maximum percent inhibition, % 1 min is the minimum percent inhibition, radiolabel is the probe, and the $K_d$ is the apparent dissociation constant for the radioligand for the receptor as determined by Hot saturation experiments.

RECOMBINANT RECEPTOR FUNCTIONAL ASSAY: Cells were plated in complete growth medium at 85,000 cells/well in 96-well poly-D-lysine coated plates (Corning) and cultured for ~19 h before assay. Cells were washed with PBS and then incubated with inhibitor for 30 min at 37° C. and 95% humidity in Cellgro Complete Serum-Free/Low-Protein medium (Mediatech, Inc.) with L-glutamine and 1 g/L BSA. Isobutyl-methylxanthine was added to the cells at a concentration of 300 □M and incubated for 30 min at 37° C. Human □-CGRP was added to the cells at a concentration of 0.3 nM and allowed to incubate at 37° C. for 5 min. After □-CGRP stimulation the cells were washed with PBS and processed for cAMP determination utilizing the two-stage assay procedure according to the manufacturer's recommended protocol (cAMP SPA direct screening assay system; RPA 559; Amersham Biosciences). Dose response curves were plotted and $IC_{50}$ values determined from a 4-parameter logistic fit as defined by the equation $y=((a-d)/(1+(x/c)^b)+d$, where y=response, x=dose, a=max response, d=min response, c=inflection point and b=slope.

In particular, the compounds of the following examples had activity as antagonists of the CGRP receptor in the aforementioned assays, generally with a $K_1$ or $IC_{50}$ value of less than about 50 □M.

Such a result is indicative of the intrinsic activity of the compounds in use as antagonists of CGRP receptors.

The ability of the compounds of the present invention to act as CGRP antagonists makes them useful pharmacological agents for disorders that involve CGRP in humans and animals, but particularly in humans.

The compounds of the present invention have utility in treating, preventing, ameliorating, controlling or reducing the risk of one or more of the following conditions or diseases: headache; migraine; cluster headache; chronic tension type headache; pain; chronic pain; neurogenic inflammation and inflammatory pain; neuropathic pain; eye pain; tooth pain; diabetes; non-insulin dependent diabetes mellitus; vascular disorders; inflammation; arthritis; bronchial hyperreactivity, asthma; shock; sepsis; opiate withdrawal syndrome; morphine tolerance; hot flashes in men and women; allergic dermatitis; psoriasis; encephalitis; brain trauma; epilepsy; neurodegenerative diseases; skin diseases; neurogenic cutaneous redness, skin rosaceousness and erythema; inflammatory bowel disease, irritable bowel syndrome, cystitis; and other conditions that may be treated or prevented by antagonism of CGRP receptors. Of particular importance is the acute or prophylactic treatment of headache, including migraine and cluster headache.

The subject compounds are further useful in a method for the prevention, treatment, control, amelioration, or reduction of risk of the diseases, disorders and conditions noted herein.

The subject compounds are further useful in a method for the prevention, treatment, control, amelioration, or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

For example, the present compounds may be used in conjunction with an anti-migraine agent, such as ergotamine and dihydroergotamine, or other serotonin agonists, especially a 5-$HT_{1B/1D}$ agonist, for example sumatriptan, naratriptan, zolmitriptan, eletriptan, almotriptan, frovatriptan, donitriptan, and rizatriptan, a 5-$HT_{1D}$ agonist such as PNU-142633 and a 5-$HT_{1F}$ agonist such as LY334370; a cyclooxygenase inhibitor, such as a selective cyclooxygenase-2 inhibitor, for example rofecoxib, etoricoxib, celecoxib, valdecoxib or paracoxib; a non-steroidal anti-inflammatory agent or a cytokine-suppressing anti-inflammatory agent, for example with a compound such as ibuprofen, ketoprofen, fenoprofen, naproxen, indomethacin, sulindac, meloxicam, piroxicam, tenoxicam, lomoxicaam, ketorolac, etodolac, mefenamic acid, meclofenamic acid, flufenamic acid, tolfenamiic acid, diclofenac, oxaprozin, apazone, nimesulide, nabumetone, tenidap, etanercept, tolmetin, phenylbutazone, oxyphenbutazone, diflunisal, salsalate, olsalazine or sulfasalazine and the like; or glucocorticoids. Similarly, the instant compounds may be administered with an analgesic such as aspirin, acetaminophen, phenacetin, fentanyl, sufentanil, methadone, acetyl methadol, buprenorphine or morphine.

Additionally, the present compounds may be used in conjunction with an interleukin inhibitor, such as an interleukin-1 inhibitor; an NK-1 receptor antagonist, for example aprepitant; an NMDA antagonist; an $NR_2B$ antagonist; a bradykinin-1 receptor antagonist; an adenosine A1 receptor agonist; a sodium channel blocker, for example lamotrigine; an opiate agonist such as levomethadyl acetate or methadyl acetate; a lipoxygenase inhibitor, such as an inhibitor of 5-lipoxygenase; an alpha receptor antagonist, for example indoramin; an alpha receptor agonist; a vanilloid receptor antagonist; a renin inhibitor; a granzyme B inhibitor; a substance P antagonist; an endothelin antagonist; a norepinephrin precursor; anti-anxiety agents such as diazepam, alprazolam, chlordiazepoxide and chlorazepate; serotonin $5HT_2$ receptor antagonists; opiod agonists such as codeine, hydrocodone, tramadol, dextropropoxyphene and febtanyl; an mGluR5 agonist, antagonist or potentiator; a GABA A receptor modulator, for example acamprosate calcium; nicotinic antagonists or agonists including nicotine; muscarinic agonists or antagonists; a selective serotonin reuptake inhibitor, for example fluoxetine, paroxetine, sertraline, duloxetine, escitalopram, or citalopram; an antidepressant, for example amitriptyline, nortriptyline, clomipramine, imipramine, venlafaxine, doxepin, protriptyline, desipramine, trimipramine, or imipramine; a leukotriene antagonist, for example montelukast or zafirlukast; an inhibitor of nitric oxide or an inhibitor of the synthesis of nitric oxide.

Also, the present compounds may be used in conjunction with gap junction inhibitors; neuronal calcium channel blockers such as civamide; AMPA/KA antagonists such as LY293558; sigma receptor agonists; and vitamin B2.

Also, the present compounds may be used in conjunction with ergot alkaloids other than ergotamine and dihydroergotamine, for example ergonovine, ergonovine, methylergonovine, metergoline, ergoloid mesylates, dihydroergocomine, dihydroergocristine, dihydroergocryptine, dihydro-α-ergocryptine, dihydro-β-ergocryptine, ergotoxine, ergocomine, ergocristine, ergocryptine, α-ergocryptine, β-ergocryptine, ergosine, ergostane, bromocriptine, or methysergide.

Additionally, the present compounds may be used in conjunction with a beta-adrenergic antagonist such as timolol, propanolol, atenolol, metoprolol or nadolol, and the like; a MAO inhibitor, for example phenelzine; a calcium channel blocker, for example flunarizine, diltiazem, amlodipine, felodipine, nisolipine, isradipine, nimodipine, lomerizine, verapamil, nifedipine, or prochlorperazine; neuroleptics such as olanzapine, droperidol, prochlorperazine, chlorpromazine and quetiapine; an anticonvulsant such as topiramate, zonisamide, tonabersat, carabersat, levetiracetam, lamotrigine, tiagabine, gabapentin, pregabalin or divalproex sodium; an anti-hypertensive such as an angiotensin II antagonist, for example losartan, irbesartin, valsartan, eprosartan, telmisartan, olmesartan, medoxomil, candesartan and candesartan cilexetil, an angiotensin I antagonist, an angiotensin converting enzyme inhibitor such as lisinopril, enalapril, captopril, benazepril, quinapril, perindopril, ramipril and trandolapril; or botulinum toxin type A or B.

The present compounds may be used in conjunction with a potentiator such as caffeine, an H2-antagonist, simethicone, aluminum or magnesium hydroxide; a decongestant such as oxymetazoline, epinephrine, naphazoline, xylometazoline, propylhexedrine, or levo-desoxy-ephedrine; an antitussive such as caramiphen, carbetapentane, or dextromethorphan; a diuretic; a prokinetic agent such as metoclopramide or domperidone; a sedating or non-sedating antihistamine such as acrivastine, azatadine, bromodiphenhydramine, brompheniramine, carbinoxamine, chlorpheniramine, clemastine, dexbrompheniramine, dexchlorpheniramine, diphenhydramine, doxylamine, loratadine, phenindamine, pheniramine, phenyltoloxamine, promethazine, pyrilamine, terfenadine, triprolidine, phenylephrine, phenylpropanolamine, or pseudoephedrine. The present compounds also may be used in conjunction with anti-emetics.

In a particularly preferred embodiment the present compounds are used in conjunction with an anti-migraine agent, such as: ergotamine or dihydroergotamine; a 5-HT, agonist, especially a 5-HT$_{1B/1D}$ agonist, in particular, sumatriptan, naratriptan, zolmitriptan, eletriptan, almotriptan, frovatriptan, donitriptan, avitriptan and rizatriptan, and other serotonin agonists; and a cyclooxygenase inhibitor, such as a selective cyclooxygenase-2 inhibitor, in particular, rofecoxib, etoricoxib, celecoxib, valdecoxib or paracoxib.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, solutions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glycetyl monostearate or glyceryl distearate may be employed. They may also be coated by the techniques described in the U.S. Pat. Nos. 4,256,108; 4,166,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. Similarly, transdermal patches may also be used for topical administration.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require antagonism of CGRP receptor activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are may be provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, or may be administered once or twice per day.

When treating, preventing, controlling, ameliorating, or reducing the risk of headache, migraine, cluster headache, or other diseases for which compounds of the present invention are indicated, generally satisfactory results are obtained when the compounds of the present invention are administered at a daily dosage of from about 0.1 milligram to about 100 milligram per kilogram of animal body weight, given as a single daily dose or in divided doses two to six times a day, or in sustained release form. For most large mammals, the total daily dosage is from about 1.0 milligrams to about 1000 milligrams, or from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made according to procedures known in the art or as illustrated herein.

The compounds of the present invention can be prepared readily according to the following Schemes and specific examples, or modifications thereof, using readily available starting materials, reagents and conventional synthesis procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

The synthesis of spirolactam intermediates may be conducted as described in Scheme 1. Spirolactam intermediates bearing $R^{5a}$, $R^{5b}$ and $R^{5c}$ may be prepared by employing appropriately substituted starting materials or by derivatization of any intermediates and/or final products as desired by methods known in the art.

A representative synthesis of a spirolactam intermediate is shown in Scheme 1, using a spiroazaoxindole example. 7-Azaindole (1) may be protected with a variety of protecting groups, such as the (trimethylsilyl)ethoxymethyl group shown in Scheme 1. Following the method of Marfat and Carter (*Tetrahedron Lett.*, 1987, 28, 4027-4030), treatment of 2 with pyridine hydrobromide perbromide provides the dibromoazaoxindole 3, which may be reduced to the corresponding azaoxindole 4 by reaction with zinc. The key alkylation of 4 with methyl 1,2-bis(bromomethyl)-4-benzoate (5) is carried out using cesium carbonate in DMF to afford the spiroazaoxindole 6. A variety of other bases and solvents may be employed in this alkylation reaction, and use of an alternative alkylating agent to the dibromide shown here can lead to different products. Removal of the SEM protecting group under standard conditions followed by saponification provides the acid intermediate 8. The methodology shown in Scheme 1 is not limited to azaoxindoles such as 4, but may be applied to a variety of suitably protected heterocyclic systems to give the corresponding spiro compounds.

SCHEME 1

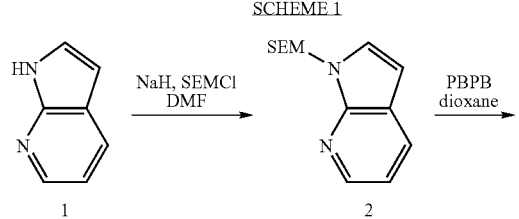

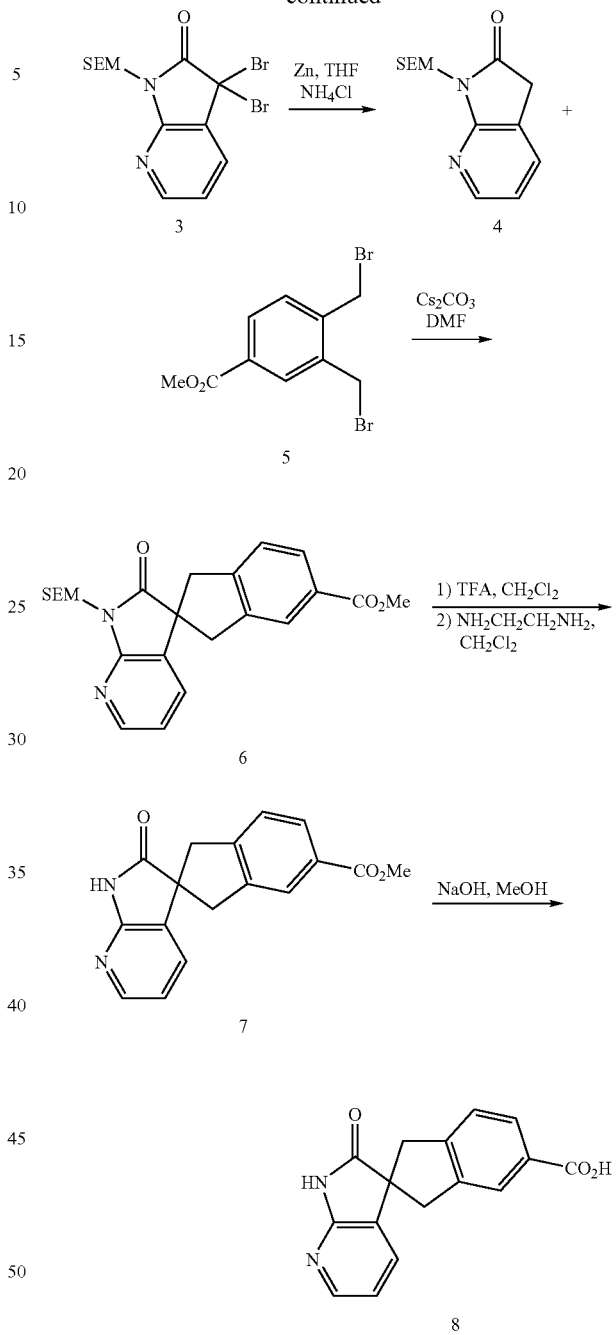

Scheme 2 details methodology that may be used to synthesize tetralin-based spirolactam intermediates. The 2,6-naphthalene diester 9 may be partially hydrogenated to give the corresponding tetrahydronaphthalene 10. Treatment of 10 with a suitable base, such as sodium bis(trimethylsilyl)amide, followed by an alkylating agent, which is allyl bromide in Scheme 2, results in substitution at the 2-position of the tetrahydronaphthalene to give compound 11. Depending upon the nature of the desired spirolactam, a number of alternative alkylating agents may be used in this step and modification of the subsequent transformations may yield a variety of final spirolactams. Oxidative cleavage of the allyl group in 11 may be effected using osmium tetroxide and sodium periodate to give the aldehyde 12. Alternative methodologies that are known to those skilled in the art, such as ozonolysis, may also be employed for this transformation. A reductive amination followed by a cyclization is used to convert 12 to the spirolactam. In Scheme 2, the aldehyde is reacted with 4-methoxybenzylamine, using sodium cyanoborohydride as reducing agent, and the resulting crude product is heated in toluene to yield the PMB-protected spirolactam 13. A variety of conditions and amines may be utilized in this step. If ammonia is used instead of the benzylamine shown, for example, subsequent cyclization may provide the unprotected lactam directly. In Scheme 2, standard deprotection methodology is used to remove the 4-methoxybenzyl substituent and saponify the methyl ester, providing the key acid intermediate 14.

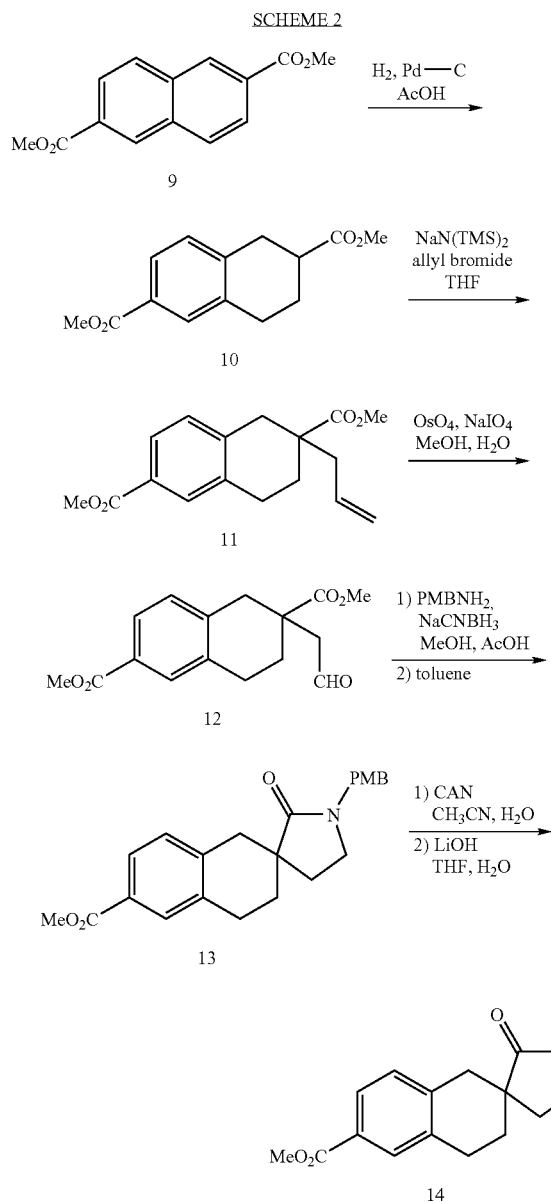

Spirolactam intermediates, such as those illustrated in Schemes 1 & 2, may be resolved to give pure enantiomers using techniques familiar to those skilled in the art. For example, chromatography of a suitable intermediate using a chiral column can be used to provide the individual enantiomers of acid intermediates such as 8 and 14. Use of standard coupling procedures using enantiomerically pure acids can provide the individual enantiomers of the final products. Resolution may be effected by other methodologies, such as fractional crystallization of diastereomeric salts, and it may be carried out on other synthetic intermediates or on the final products. Alternatively, an asymmetric synthesis of a key intermediate could be used to provide an enantiomerically enriched final product.

Spirohydantoin carboxylic acid intermediates, such as compounds 8 and 14, may be further elaborated by techniques familiar to one skilled in the art to provide the final amide products, as shown in Scheme 3.

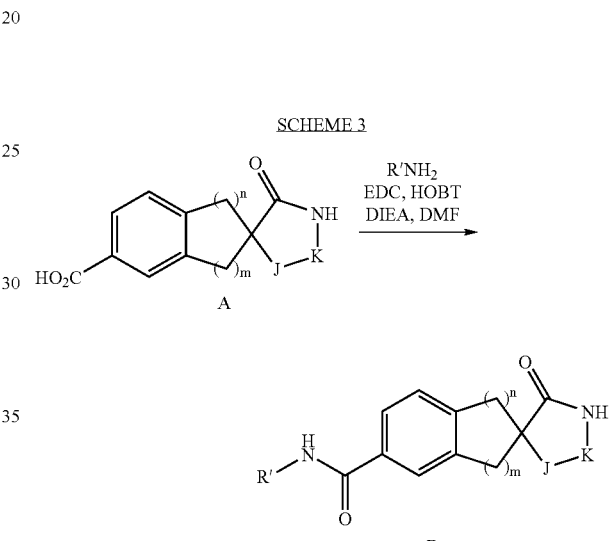

Thus, acid A may be coupled to an amine, $RNH_2$, under standard EDC-HOBT coupling conditions to provide amide B. Other standard coupling conditions may be employed in the synthesis of such amides, such as use of an alternative coupling reagent like PyBOP, or activation of the carboxylic acid as an acid anhydride or acid chloride.

Most of the amines ($RNH_2$) used to make the compounds of the present invention are readily available. They may be obtained from commercial sources or synthesized by methodology familiar to those skilled in the art and as described in the chemical literature.

Some of the amine intermediates can be prepared as outlined in Schemes 4 & 5. As shown in Scheme 4, addition of nitromethane to the known glutamic acid derived aldehyde 15 (*Tetrahedron Asymmetry* 1998, 3381-3394), followed by in situ elimination affords nitro olefin 16. Addition of the aryl group via a boronic acid derivative, or similar equivalent, can be accomplished in a stereoselective manner through chiral ligand-Rh catalysis. Concomitant nitro reduction and benzyl ester hydrogenolysis affords the amino acid 18. Ring closure under standard conditions, followed by removal of a single tert-butoxycarbonyl group furnishes the lactam 20. Intermediates such as 18 can be further processed as in Scheme 5.

SCHEME 4
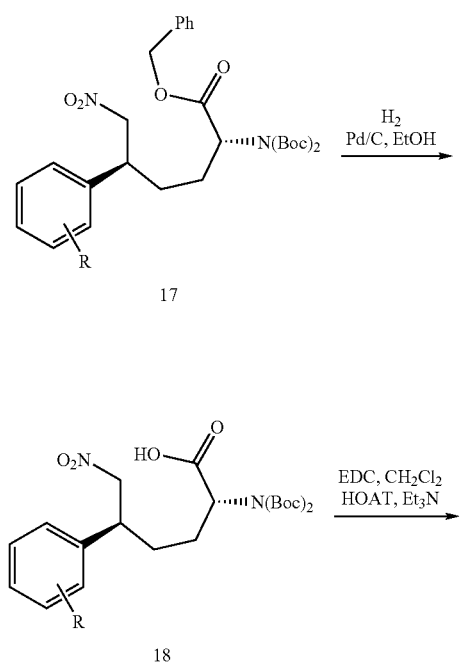
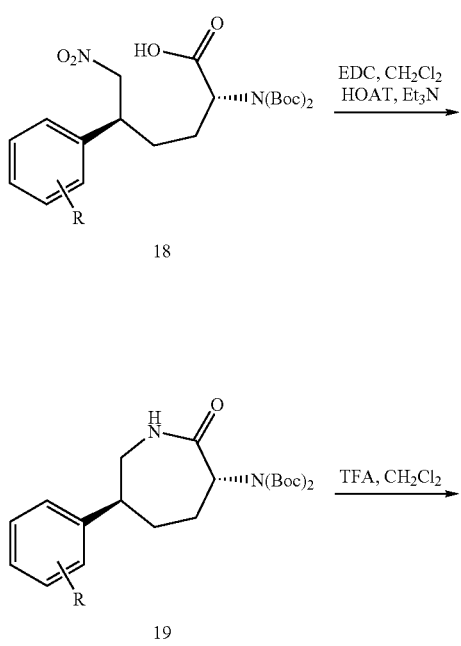
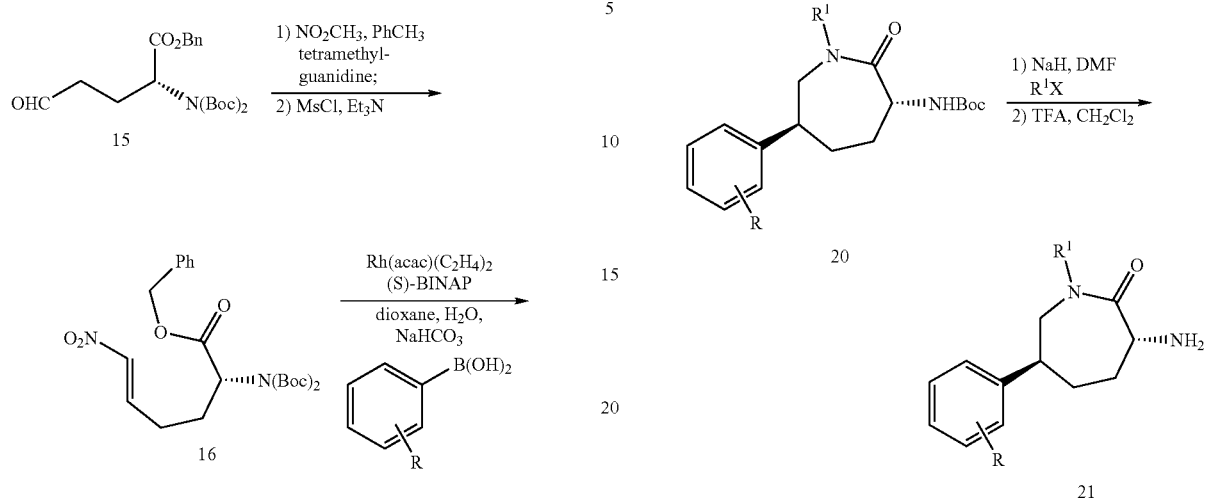
Alternatively, amino acid 18 can be alkylated, either reductively or via an $S_N2$ displacement, to afford intermediates such as 22 (Scheme 5). Ring closure under standard conditions, followed by protecting group removal furnishes the lactam 24.
SCHEME 5
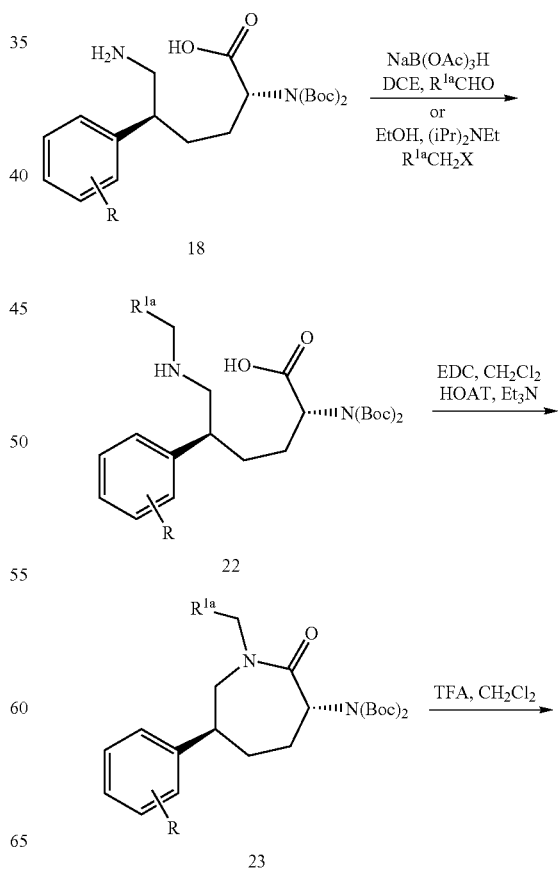

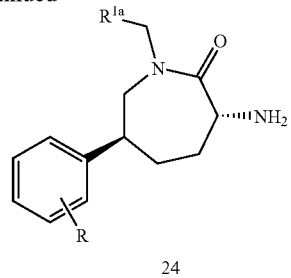

24

Fused imidazoles are prepared as shown in Scheme 6. Thioamide 25 is reacted with a variety of amino alcohols 26 in the prescence of mercury (II) chloride to give amidines 27. Oxidation of the alcohol with concommitant ring closure using either the Dess-Martin periodinane or pyridinium dichromate finally yields imidazoles of the general formula 28.

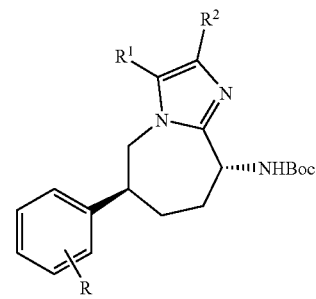

28

Triazole derivatives are prepared as shown in Scheme 7. Addition of hydrazine to thioamide 25 gives the corresponding hydrazide 29. Various carboxylic acids or acid chlorides can undergo couplings under standard conditions affording after ring closure the desired fused triazoles 30.

SCHEME 6

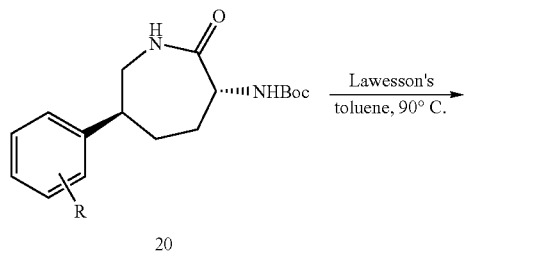

20

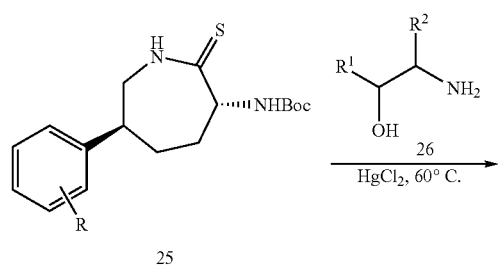

25

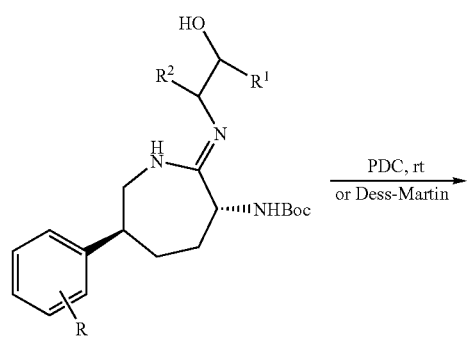

27

SCHEME 7

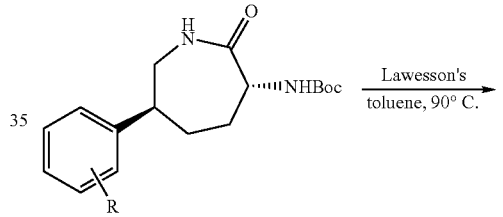

20

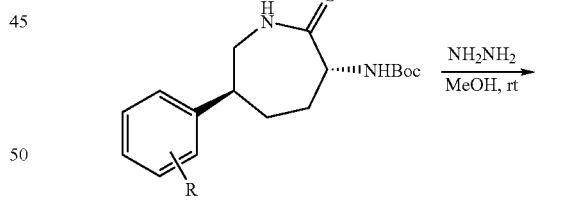

25

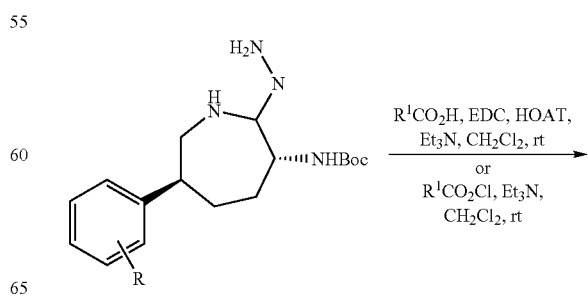

29

-continued

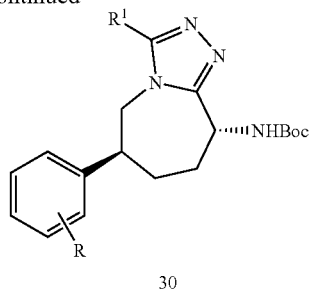

30

In some cases the final product B (Scheme 3) may be further modified, for example, by manipulation of substituents. These manipulations may include, but are not limited to, reduction, oxidation, alkylation, acylation, and hydrolysis reactions which are commonly known to those skilled in the art.

In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

INTERMEDIATE 1

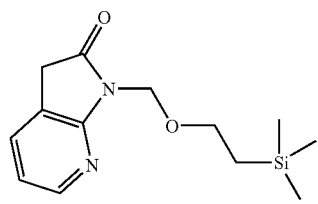

1-{[2-(Trimethylsilyl)ethoxy]methyl}-1,3-dihydro-2H-pyrrolo[2,3-b]pyridin-2-one

Step A. 1-{[2-Trimethylsilyl)ethoxy]methyl}-1H-pyrrolo[2,3-h]pyridine

Sodium hydride (60% dispersion in mineral oil; 16.2 g, 0.404 mol) was added in portions over 25 min to a solution of 7-azaindole (39.8 g, 0.337 mol) in DMF (200 mL) at 0 □C and the mixture was stirred for 1 h. 2-(Trimethylsilyl)ethoxymethyl chloride (71.8 mL, 0.404 mol) was then added slowly over 15 min, keeping the temperature of the reaction mixture below 10 □C. After 1 h, the reaction was quenched with $H_2O$ (500 mL) and the mixture was extracted with $CH_2Cl_2$ (5×300 mL). The combined organic layers were washed with brine, dried over $MgSO_4$, filtered, concentrated and dried under high vacuum to give the title compound. MS: m/z=249 (M+1).

Step B. 3,3-Dibromo-1-{[2-(trimethylsilyl)ethoxy]methyl}-1,3-dihydro-2H-pyrrolo[2,3-b]pyridin-2-one A solution of 1-{[2-(trimethylsilyl)ethoxy]methyl}-1H-pyrrolo[2,3-b]pyridine from Step A (43.1 g, 0.174 mol) in dioxane (300 mL) was added dropwise over 30 min to a suspension of pyridine hydrobromide perbromide (277 g, 0.868 mol) in dioxane (300 mL). The reaction was stirred at ambient temperature using an overhead mechanical stirrer. After 60 min, the biphasic reaction mixture was quenched with $H_2O$ (300 mL) and extracted with EtOAc. The aqueous layer was washed with EtOAc (2×300 mL) and the combined organic layers were washed with $H_2O$ (4×300 mL; the final wash was pH 5-6), then brine (300 mL), then dried over $MgSO_4$, filtered and concentrated under reduced pressure. The crude product was immediately dissolved in $CH_2Cl_2$ and the solution filtered through a plug of silica, eluting with $CH_2Cl_2$ until the dark red color had completely eluted from the plug. The filtrate was washed with saturated aqueous $NaHCO_3$ (400 mL), then brine (400 mL), dried over $MgSO_4$ and concentrated in vacuo to give the title compound. MS: m/z=423 (M+1).

Step C. 1-{[2-(Trimethylsilyl)ethoxy]methyl}-1,3-dihydro-2H-pyrrolo[2,3-b]pyridin-2-one Zinc (100 g, 1.54 mol) was added to a solution of 3,3-dibromo-1-{[2-(trimethylsilyl)ethoxy]methyl}-1,3-dihydro-2H-pyrrolo[2,3-b]pyridin-2-one from Step B (65 g, 0.154 mol) in THF (880 mL) and saturated aqueous ammonium chloride (220 mL). After 3 h, the reaction was filtered and concentrated in vacuo. The residue was partitioned between EtOAc and $H_2O$ which resulted in the formation of a white precipitate. Both layers were filtered through a Celite pad and the layers were separated. The aqueous layer was washed with EtOAc (2×) and the combined organic layers were washed with $H_2O$, dried over $MgSO_4$, filtered, and concentrated. The crude product was filtered through a plug of silica gel eluting with $CH_2Cl_2$:EtOAc—90:10 and the eluant was concentrated under reduced pressure to provide the title compound. MS: m/z=265 (M+1).

INTERMEDIATE 2

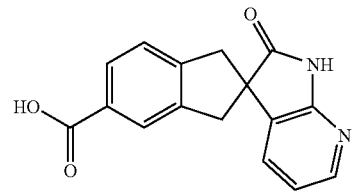

(±)-2'-Oxo-1,1',2',3-tetrahydrospiro[indene-2,3'-pyrrolo[2,3-b]pyridine]-5-carboxylic acid Step A. (±)-Methyl 2'-oxo-1'-{[2-(trimethylsilyl)ethoxy]methyl}-1,1',2',3-tetrahydrospiro[indene-2,3'-pyrrolo[2,3-b]pyridine]-5-carboxylate To a solution of methyl 1,2-bis(bromomethyl)-4-benzoate (9.20 g, 28.6 mmol) and 1-{[2-(trimethylsilyl)ethoxy]methyl}-1,3-dihydro-2H-pyrrolo[2,3-b]pyridin-2-one (7.55 g, 28.6 mmol, described in Intermediate 1) in DMF (70 mL) was added cesium carbonate (9.78 g, 30.0 mmol). After 4 h the reaction mixture was partitioned between $Et_2O$ (100 mL) and $H_2O$ (100 mL). The aqueous layer was extracted further with $Et_2O$ (2×100 mL). The combined organic layers were washed with $H_2O$ (2×100 mL), then brine (100 mL), then dried over $MgSO_4$, filtered, and concentrated under reduced pressure. The crude product was purified by silica gel chromatography, eluting with a gradient of hexane:EtOAc—85:15 to 70:30, to give the title compound. MS: m/z=425 (M+1).

Step B. (±)-2'-Oxo-1,1',2',3-tetrahydrospiro[indene-2,3'-pyrrolo[2,3-b]pyridine]-5-carboxylic acid To a solution of (±)-methyl 2'-oxo-1'-{[2-(trimethylsilyl)ethoxy]methyl}-1,1',2',3-tetrahydrospiro[indene-2,3'-pyrrolo[2,3-b]pyridine]-5-carboxylate from Step B (3.65 g, 8.60 mmol) in $CH_2Cl_2$ (80 mL) was added $CF_3CO_2H$ (40 mL, 52 mmol) and the resulting mixture was stirred at ambient temperature for 18 h, then concentrated in vacuo. The residue was dissolved in $CH_2Cl_2$ (100 mL) and treated with ethylene diamine (2.3 mL, 34.4 mmol). The reaction mixture was stirred at ambient temperature for 18 h, then diluted with saturated aqueous $NaHCO_3$ (50 mL). The organic layer was removed and the aqueous layer was extracted further with $CH_2Cl_2$ (2×100 mL). The combined organic layers were washed with brine (50 mL), then dried over $MgSO_4$, filtered, and concentrated in vacuo. The crude product was purified by silica gel chromatography, eluting with $CH_2Cl_2$:MeOH—97:3, to give methyl 2'-oxo-1,1',2',3-tetrahydrospiro[indene-2,3'-pyrrolo[2,3-b]pyridine]-5-carboxylate as a tan solid. This solid was dissolved in MeOH (22 mL) and 1 N sodium hydroxide (25.4 mL, 25.4 mmol) was added. The reaction mixture was heated at 60° C. for 18 h then allowed to cool. The mixture was acidified by addition of 6 N HCl, and the resulting precipitate was isolated by filtration, washed with $H_2O$, and dried in vacuo to give the title compound. MS: m/z=281 (M+1).

INTERMEDIATE 3

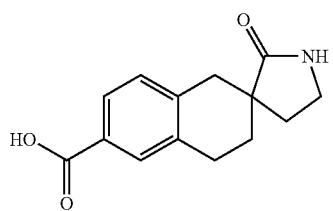

(±)-2'-Oxo-3,4-dihydro-1H-spiro[naphthalene-2,3'-pyrrolidine]-6-carboxylic acid

Step A. (±)-Dimethyl 1,2,3,4-tetrahydronaphthalene-2,6-dicarboxylate

A mixture of dimethyl naphthalene-2,6-dicarboxylate (25.0 g, 102 mmol) and 5% Pd—C (5.0 g) in AcOH (75 mL) was shaken under an atmosphere of hydrogen (ca. 150 p.s.i.) at 80° C. for 6 h. The reaction mixture was cooled, purged with argon, and filtered through a pad of Celite, washing with AcOH. The filtrate was concentrated under reduced pressure to give the title compound. MS: m/z=249 (M+1).

Step B. (±)-Dimethyl 2-allyl-1,2,3,4-tetrahydronaphthalene-2,6-dicarboxylate To a stirred solution of (±)-dimethyl 1,2,3,4-tetrahydronaphthalene-2,6-dicarboxylate from Step A (10.0 g, 40.4 mmol) in THF (200 mL) at −70° C. was added sodium bis(trimethylsilyl)amide (1.0 M in THF, 45 mL, 45 mmol) dropwise, over 10 min, such that the reaction temperature was maintained below −65° C. during the addition. The mixture was stirred at −70° C. for a further 40 min, then allyl bromide (5.87 g, 48.5 mmol) was added dropwise over 3 min. Stirring was continued at −70° C. for 2 h, then the mixture was partitioned between $H_2O$ (300 mL) and EtOAc (300 mL). The aqueous phase was extracted further with EtOAc (2×300 mL), and the combined organic extracts were washed with brine (100 mL), dried over $Na_2SO_4$, filtered, and concentrated in vacuo. The crude product was purified by silica gel chromatography, eluting with a gradient of hexane:EtOAc—100:0 to 0:100, to give the title compound. MS: m/z=289 (M+1).

Step C. (±)-Dimethyl 2-(2-oxoethyl)-1,2,3,4-tetrahydronaphthalene-2,6-dicarboxylate To a stirred solution of (±)-dimethyl 2-allyl-1,2,3,4-tetrahydronaphthalene-2,6-dicarboxylate from Step B (433 mg, 1.50 mmol) in MeOH (20 mL) and $H_2O$ (7 mL) was added osmium tetroxide (2.5 wt. % in t-BuOH, 1.07 mL, 0.105 mmol) and sodium periodate (964 mg, 4.51 mmol). The resulting mixture was stirred for 1 h at ambient temperature and a thick white precipitate quickly formed. After 70 min, the mixture was partitioned between dilute aqueous NaCl (100 mL) and EtOAc (200 mL). The organic layer was dried over $Na_2SO_4$, filtered, and concentrated in vacuo to give the title compound in sufficient purity for use in the next step. MS: m/z=291 (M+1).

Step D. (±)-Dimethyl 2-{2-[(4-methoxybenzyl)amino]ethyl}-1,2,3,4-tetrahydronaphthalene-2,6-dicarboxylate A solution of (1)-dimethyl 2-(2-oxoethyl)-1,2,3,4-tetrahydronaphthalene-2,6-dicarboxylate from Step C (436 mg, 1.50 mmol), 4-methoxybenzylamine (247 mg, 1.80 mmol), and AcOH (0.206 mL, 3.60 mmol) was stirred in MeOH (10 mL) at ambient temperature for 5 min, then sodium cyanoborohydride (113 mg, 1.80 mmol) was added. After 18 h, the mixture was concentrated in vacuo, and the residue was partitioned between saturated aqueous $NaHCO_3$ (10 mL) and $CH_2Cl_2$ (20 mL). The aqueous phase was extracted further with $CH_2Cl_2$ (10 mL), and the combined organic extracts were dried over $Na_2SO_4$, filtered, and concentrated in vacuo to give the title compound in sufficient purity for use in the next step. MS: m/z=412 (M+1).

Step E. (±)-Methyl 1'-(4-methoxybenzyl)-2'-oxo-3,4-dihydro-1H-spiro[naphthalene-2,3'-pyrrolidine]-6-carboxylate A solution of (±)-dimethyl 2-{2-[(4-methoxybenzyl)amino]ethyl}-1,2,3,4-tetrahydronaphthalene-2,6-dicarboxylate from Step D (618 mg, 1.50 mmol) in toluene (20 mL) was heated at reflux for 10 min, then allowed to cool and the solvent was removed in vacuo. The crude product was purified by silica gel chromatography, eluting with a gradient of hexane:EtOAc—100:0 to 0:100, to give the title compound. MS: m/z=380 (M+1).

Step F. (±)-Methyl 2'-oxo-3,4-dihydro-1H-spiro[naphthalene-2,3'-pyrrolidine]-6-carboxylate To a stirred solution of (±)-methyl 1'-(4-methoxybenzyl)-2'-oxo-3,4-dihydro-1H-spiro[naphthalene-2,3'-pyrrolidine]-6-carboxylate from Step E (270 mg, 0.712 mmol) in $CH_3CN$ (9 mL) was added dropwise a solution of ceric ammonium nitrate (1.95 g, 3.56 mmol) in $H_2O$ (9 mL). The resulting mixture was stirred at ambient temperature for 18 h, then at 50° C. for 4 h, then allowed to cool. The $CH_3CN$ was removed under reduced pressure, and the residual mixture was partitioned between dilute aqueous $NaHCO_3$ (100 mL) and EtOAc (200 mL). The organic extract was dried over Na₂SO₄, filtered, and concentrated in vacuo. The residue was triturated with EtOAc to give the title compound. MS: m/z=260 (M+1).

Step G. (±)-2'-Oxo-3,4-dihydro-1H-spiro[naphthalene-2,3'-pyrrolidine]-6-carboxylic acid A stirred solution of (±)-methyl 2'-oxo-3,4-dihydro-1H-spiro[naphthalene-2,3'-pyrrolidine]-6-carboxylate from Step F (50 mg, 0.193 mmol) and lithium hydroxide (24 mg, 0.578 mmol) in THF (3 mL) and H₂O (1 mL) was heated at reflux for 5 h, then allowed to cool. The mixture was poured into 10% aqueous HCl (10 mL) and extracted with EtOAc (3×20 mL), and the combined organic extracts were dried over Na₂SO₄, filtered, and concentrated in vacuo. The residue was triturated with CH₂Cl₂ to give the title compound. MS: m/z=246 (M+1).

INTERMEDIATE 4

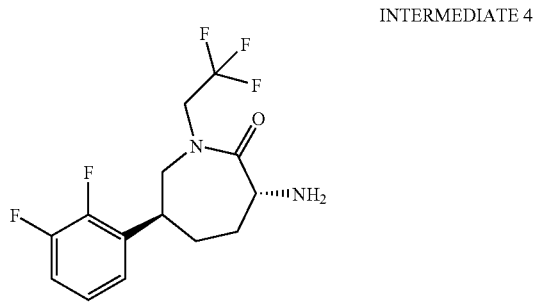

(3R,6S)-3-Amino-6-(2,3-difluorophenyl)-1-(2,2,2-trifluoroethyl)azepan-2-one

Step A. 1-Benzyl 5-methyl N,N-bis(tert-butoxycarbonyl)-D-glutamate

To a solution of Boc-D-Glu-OBn (50.0 g, 148 mmol) in CH₂Cl₂ (400 mL) and MeOH (100 mL) at 0° C. was added (trimethylsilyl)diazomethane (2.0 M in hexanes, 89 mL, 118 mmol) dropwise via an addition funnel. After 1 h the reaction was concentrated under reduced pressure. This residue was diluted with CH₃CN (400 mL) and di-tert-butyl dicarbonate (48.5 g, 222 mmol) was added, followed by DMAP (18.1 g, 14.8 mmol). The mixture was stirred at ambient temperature for 24 h, then concentrated in vacuo. The crude product was purified by silica gel chromatography, eluting with a gradient of hexane:EtOAc—90:10 to 40:60, to give the title compound. MS: m/z=252 (M-C₁₀H₁₅O₄).

Step B. Benzyl (2R,5E)-2-[bis(tert-butoxycarbonyl) amino]-6-nitrohex-5-enoate

To a stirred solution of 1-benzyl 5-methyl N,N-bis(tert-butoxycarbonyl)-D-glutamate from Step A (48.2 g, 106.8 mmol) in Et₂O (400 mL), at −78° C., was added DIBAL (1.0 M in toluene, 133 mL, 133 mmol) slowly so as not to let the internal temperature exceed −65° C. After 15 min, an additional portion of DIBAL (20 mL, 20 mmol) was added. After stirring for a further 20 min, H₂O (300 mL) was added and the reaction was warmed to ambient temperature and stirred for 30 min. This mixture was diluted with Et₂O and H₂O, the layers separated and the aqueous phase extracted with more Et₂O. The combined organic extracts were washed with saturated aqueous sodium potassium tartrate (2×), then brine, then dried over MgSO₄, filtered and concentrated in vacuo to give benzyl N,N-bis(tert-butoxycarbonyl)-5-oxo-D-norvalinate. This material was dissolved in toluene (310 mL) and nitromethane (57.1 mL, 1.05 mol) and 1,1,3,3-tetramethylguanidine (1.3 mL, 10.5 mmol) were added at 0° C. After stirring for 30 min the nitroaldol reaction was complete, and methanesulfonyl chloride (12.2 mL, 158 mmol) was added, followed by triethylamine (22.0 mL, 158 mmol) at 0° C. and the reaction mixture was allowed to warm to ambient temperature. After 1 h, additional methanesulfonyl chloride (3 mL, 39 mmol) and triethylamine (5.5 mL, 39 mmol) were added. The mixture was stirred for an additional 30 min, then diluted with Et₂O and aqueous NaHCO₃. The phases were separated and the aqueous layer was extracted further with Et₂O. The combined organic extracts were dried over MgSO₄, filtered and concentrated in vacuo. The crude product was purified by silica gel chromatography, eluting with a gradient of hexane:EtOAc—95:5 to 50:50, to give the title compound. MS: m/z=487 (M+Na).

Step C. Benzyl (5S)—N,N-bis(tert-butoxycarbonyl)-5-(2,3-difluorophenyl)-6-nitro-D-norleucinate A solution of benzyl (2R,5E)-2-[bis(tert-butoxycarbonyl) amino]-6-nitrohex-5-enoate from Step B (34.0 g, 73.2 mmol), 2,3-difluorophenylboronic acid (28.9 g, 183 mmol) and water (4.62 mL, 256 mmol) in dioxane (240 mL) was degassed with argon for 15 min. To this solution was added sodium bicarbonate (3.08 g, 36.6 mmol), (S)-BINAP (1.28 g, 2.05 mmol) and acetylacetanotobis(ethylene)rhodium(I) (0.472 g, 1.83 mmol). The mixture was stirred at ambient temperature for 2 min then heated to 35° C. After 4 h, (S)-BINAP (255 mg, 0.41 mmol) and acetylacetanotobis(ethylene)rhodium(I) (94 mg, 0.36 mmol) were added. After an additional 2 h, the reaction was partitioned between CH₂Cl₂ and aqueous NaHCO₃. The aqueous layer was extracted with another portion of CH₂Cl₂. The combined organic extracts were dried over MgSO₄, filtered and concentrated in vacuo. The crude product was purified by silica gel chromatography, eluting with a gradient of hexane:EtOAc—95:5 to 40:60, to give the title compound. MS: m/z=379 (M-C₁₀H₁₅O₄).

Step D. (5S)—N²,N²-Bis(tert-butoxycarbonyl)-5-(2,3-difluorophenyl)-D-lysine

A mixture of benzyl (5S)—N²,N²-bis(tert-butoxycarbonyl)-5-(2,3-difluorophenyl)-6-nitro-D-norleucinate from Step C (15.5 g, 26.8 mmol) and 10% Pd/C (12.0 g) in EtOH (175 mL), was hydrogenated at 55 psi for 18 h. An additional portion of 10% Pd/C (4.0 g) was added and the reaction mixture was hydrogenated at 55 psi for a further 18 h. The reaction mixture was filtered through Celite, washing with EtOH, and the filtrate was concentrated in vacuo to afford the title compound. MS: m/z=459 (M+1).

Step E. tert-Butyl (3R,6S)-6-(2,3-difluorophenyl)-2-oxoazepan-3-ylcarbamate

To a solution (5S)—N²,N²-bis(tert-butoxycarbonyl)-5-(2,3-difluorophenyl)-D-lysine from Step D (22.0 g, 48.0 mmol)

in CH$_2$Cl$_2$ (700 mL) were added EDC (11.0 g, 57.6 mmol) and HOAT (3.27 g, 24.0 mmol) followed by triethylamine (10.0 mL, 72.0 mmol). After 1 h, aqueous NaHCO$_3$ was added, the layers were separated, and the aqueous phase was extracted with CH$_2$Cl$_2$. The combined organic extracts were dried over MgSO$_4$, filtered and concentrated in vacuo. The residue was purified by silica gel chromatography, eluting with CH$_2$Cl$_2$:MeOH—90:10, to give the title compound. MS: m/z=341 (M+1).

Step F: tert-Butyl (3R,6S)-6-(2,3-difluorophenyl)-2-oxo-1-(2,2,2-trifluoroethyl)azepan-3-ylcarbamate Sodium hydride (60% dispersion in mineral oil, 70.7 mg, 1.06 mmol) was added to a solution of tert-butyl (3R,6S)-6-(2,3-difluorophenyl)-2-oxoazepan-3-ylcarbamate from Step E (301 mg, 0.884 mmol) in DMF (7 mL) at –35° C. After 15 min, 2,2,2-trifluoroethyl trichloromethanesulfonate (0.314 mL, 1.91 mmol) was added and stirring was continued at –35° C. After 30 min, additional sodium hydride (27 mg, 0.40 mmol) and 2,2,2-trifluoroethyl trichloromethanesulfonate (0.140 mL, 0.85 mmol) were added. After 2 h, the reaction was quenched with H$_2$O and the mixture was extracted with EtOAc. The organic layer was washed with water (3×), then brine, then dried over MgSO$_4$, filtered and concentrated in vacuo. The residue was purified by silica gel chromatography, eluting with a gradient of hexane:EtOAc—100:0 to 70:30, to give the title compound. MS: m/z=423 (M+1).

Step G: (3R,6S)-3-Amino-6-(2,3-difluorophenyl)-1-(2,2,2-trifluoroethyl)azepan-2-one To a solution of tert-butyl (3R,6S)-6-(2,3-difluorophenyl)-2-oxo-1-(2,2,2-trifluoroethyl)azepan-3-ylcarbamate from Step F (135 mg, 0.320 mmol) in CH$_2$Cl$_2$ (5 mL) was added CF$_3$CO$_2$H (2.5 mL). After 30 min, the solution was concentrated in vacuo and azeotroped with toluene (2×). Saturated aqueous NaHCO$_3$ was added and the mixture was extracted with CH$_2$Cl$_2$ (3×). The combined organic extracts were washed with brine, dried over MgSO$_4$, filtered and concentrated in vacuo to give the title compound. MS: m/z=323 (M+1).

INTERMEDIATE 5

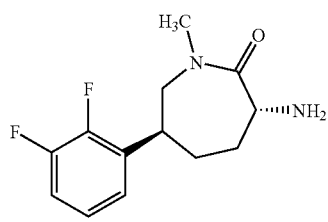

(3R,6S)-3-Amino-6-(2,3-difluorophenyl)-1-methylazepan-2-one

Essentially following the procedures outlined for the preparation of Intermediate 4, but using iodomethane in place of 2,2,2-trifluoroethyl trichloromethanesulfonate, the title compound was prepared. MS: m/z=255 (M+1).

INTERMEDIATE 6

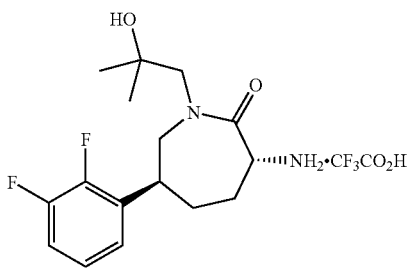

(3R,6S)-3-Amino-6-(2,3-difluorophenyl)-1-(2-hydroxy-2-methylpropyl)azepan-2-one, trifluoroacetic acid salt Step A. Di-tert-butyl[(3R,6S)-6-(2,3-difluorophenyl)-1-(2-hydroxy-2-methylpropyl)-2-oxoazepan-3-yl]imidodicarbonate A mixture of (5S)-N$^2$,N$^2$-bis(tert-butoxycarbonyl)-5-(2,3-difluorophenyl)-D-lysine (0.569 g, 1.24 mmol, described in Intermediate 4), 1-chloro-2-methyl-2-propanol (0.202 g, 1.86 mmol) and N,N-diisopropylethylamine (0.713 mL, 4.10 mmol) in EtOH (5 mL) was heated at 75° C. for 18 h. The reaction mixture was concentrated to dryness under reduced pressure and the residue was dissolved in CH$_2$Cl$_2$ (20 mL), then EDC (0.358 g, 1.87 mmol), HOAT (0.252 g, 1.87 mmol) and N,N-diisopropylethylamine (0.650 mL, 3.73 mmol) were added. The resulting mixture was stirred at ambient temperature for 18 h, then aqueous NaHCO$_3$ was added. The layers were separated and the aqueous phase was extracted with CH$_2$Cl$_2$. The combined organic extracts were dried over MgSO$_4$, filtered, and concentrated in vacuo. The residue was purified by silica gel chromatography, eluting with a gradient of hexane:EtOAc—90:10 to 65:35, to give the title compound. MS: m/z=513 (M+1).

Step B. (3R,6S)-3-Amino-6-(2,3-difluorophenyl)-1-(2-hydroxy-2-methylpropyl)azepan-2-one, trifluoroacetic acid salt To a solution of di-tert-butyl[(3R,6S)-6-(2,3-difluorophenyl)-1-(2-hydroxy-2-methylpropyl)-2-oxoazepan-3-yl]imidodicarbonate from Step A (0.095 g, 0.185 mmol) in CH$_2$Cl$_2$ (10 mL) was added CF$_3$CO$_2$H (3 mL). After 1 h, the solution was concentrated in vacuo to give the title compound. MS: m/z=313 (M+1).

INTERMEDIATE 7

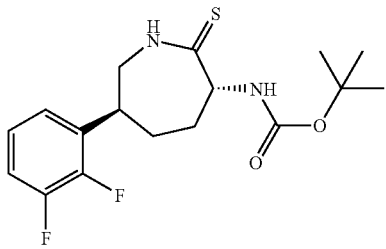

tert-Butyl (3R,6S)-6-(2,3-difluorophenyl-2-thioxoazepan-3-ylcarbamate

Lawesson's reagent [2,4-bis(4-methoxyphenyl)-2,3-dithia-2,4-diphosphetane-2,4-disulfide] (2.90 g, 7.18 mmol) was added to a suspension of tert-butyl (3R,6S)-6-(2,3-difluorophenyl)-2-oxoazepan-3-ylcarbamate (4.79 g, 14.1 mmol, described in Intermediate 4) in toluene (250 mL) and the mixture was heated to 90° C. After 1 h, the reaction was allowed to cool to ambient temperature and concentrated under reduced pressure. The residue was partially purified by silica gel chromatography, eluting with a gradient of $CH_2Cl_2$: EtOAc—100:0 to 85:15. Further purification by silica gel chromatography, eluting with a gradient of hexane:EtOAc—80:20 to 70:30 afforded the title compound. MS: m/z=357 (M+1).

INTERMEDIATE 8

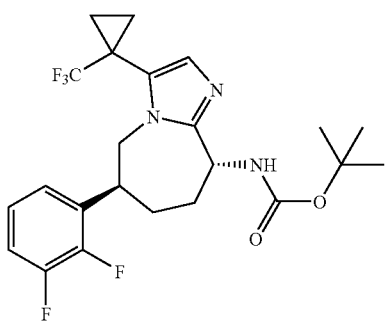

tert-Butyl{(6S,9R)-6-(2,3-difluorophenyl)-3-[1-(trifluoromethyl)cyclopropyl]-6,7,8,9-tetrahydro-5H-imidazo[1,2-a]azepin-9-yl}carbamate Step A: tert-Butyl[(2Z,3R,6S)-6-(2,3-difluorophenyl)-2-({2-hydroxy-2-[1-(trifluoromethyl)cyclopropyl]ethyl}imino)azepan-3-yl]carbamate Mercury(II) chloride (149 mg, 0.547 mmol) was added to a solution of tert-butyl [(3R,6S)-6-(2,3-difluorophenyl)-2-thioxoazepan-3-yl]carbamate (150 mg, 0.421 mmol, described in Intermediate 7), and 2-amino-1-[1-(trifluoromethyl)cyclopropyl]ethanol (569 mg, 3.367 mmol) in ethanol (5 mL) at 60° C. After 10 min, the reaction was allowed to cool to ambient temperature. The mixture was filtered and concentrated under reduced pressure. Saturated aqueous $NaHCO_3$ was added and the mixture was extracted with $CH_2Cl_2$ (3×). The combined organic extracts were dried over $MgSO_4$, filtered, and concentrated under reduced pressure to give the title compound. MS: m/z=492 (M+1).

Step B: tert-Butyl{(6S,9R)-6-(2,3-difluorophenyl)-3-[1-(trifluoromethyl)cyclopropyl]-6,7,8,9-tetrahydro-5H-imidazo[1,2-a]azepin-9-yl}carbamate Pyridinium dichromate (765 mg, 2.035 mmol) was added to a solution of crude tert-butyl [(2Z,3R,6S)-6-(2,3-difluorophenyl)-2-({2-hydroxy-2-[1-(trifluoromethyl)cyclopropyl]ethyl}imino)azepan-3-yl]carbamate from Step A (200 mg, 0.407 mmol) in acetonitrile (5 mL). After 70 h at ambient temperature, the mixture was filtered and concentrated. Saturated aqueous $NaHCO_3$ was added and the mixture was extracted with $CH_2Cl_2$ (3×). The combined organic extracts were dried over $MgSO_4$, filtered, and concentrated under reduced pressure to give the title compound. MS: m/z=472 (M+1).

INTERMEDIATES 9-10

Essentially following the procedures outlined for Intermediate 2, the compounds listed in Table 1 were prepared. The requisite starting materials were commercially available, described in the literature, synthesized according to methodology described herein, or readily synthesized by one skilled in the art of organic synthesis.

TABLE 1

| Intermediate | R¹ | R² | MS (M + 1) |
|---|---|---|---|
| 9 | (sec-butyl) | H | 392 |
| 10 | (tert-butoxy) | H | 436 |

INTERMEDIATE 11

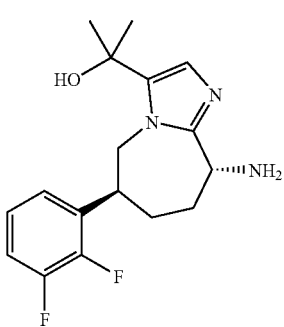

2-[(6S,9R)-9-Amino-6-(2,3-difluorophenyl)-6,7,89-tetrahydro-5H-imidazo[1,2-a]azepin-3-yl]propan-2-ol Concentrated sulfuric acid (0.335 mL, 5.70 mmol) was added to a solution of tert-butyl [(6S,9R)-6-(2,3-difluorophenyl)-3-(1-methoxy-1-methylethyl)-6,7,8,9-tetrahydro-5H-imidazo[1,2-a]azepin-9-yl]carbamate (310 mg, 0.712 mmol) in H$_2$O (2 mL) and the mixture heated to 60° C. After 2.5 h, the reaction mixture was quenched with saturated aqueous NaHCO$_3$. The mixture was extracted with CH$_2$Cl$_2$ (3×), and the combined organic extracts were washed with water, saturated brine, dried over Na$_2$SO$_4$, filtered and concentrated under reduced pressure to give the title compound. MS: m/z=322 (M+1).

INTERMEDIATE 12

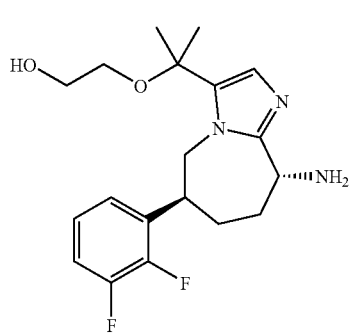

2-{1-[(6S,9R)-9-Amino-6-(2,3-difluorophenyl)-6,7,8,9-tetrahydro-5H-imidazo[1,2-a]azepin-3-yl]-1-methylethoxy}ethanol Essentially following the procedures outlined for the preparation of Intermediate 11, but using ethylene glycol in place of H$_2$O, the title compound was obtained. MS: m/z=366 (M+1).

INTERMEDIATE 13

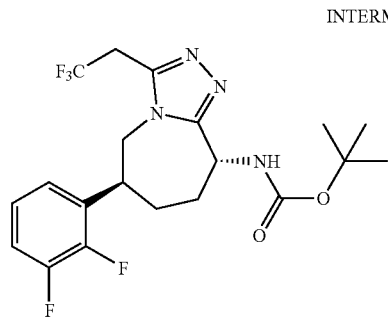

tert-Butyl (6S,9R)-6-(2,3-difluorophenyl)-3-(2,2,2-trifluoroethyl)-6,7,8,9-tetrahydro-5H-[1,2,4]triazolo[4,3-a]azepin-9-ylcarbamate Step A: tert-Butyl (3R,6S)-6-(2,3-difluorophenyl)-2-hydrazonoazepan-3-ylcarbamate Hydrazine monohydrate (2.23 mL, 46.0 mmol) was added to a solution of tert-butyl (3R,6S)-6-(2,3-difluorophenyl)-2-thioxoazepan-3-ylcarbamate (546 mg, 1.53 mmol) in methanol (25 mL). After 30 min, the mixture was concentrated under reduced pressure. Saturated aqueous NaHCO$_3$ was added and the mixture was extracted with CH$_2$Cl$_2$ (3×). The combined organic extracts were dried over Na$_2$SO$_4$, filtered, and concentrated under reduced pressure to give the title compound. MS: m/z=355 (M+1).

Step B: tert-Butyl (6S,9R)-6-(2,3-difluorophenyl)-3-(2,2,2-trifluoroethyl)-6,7,8,9-tetrahydro-5H-[1,2,4]triazolo[4,3-a]azepin-9-ylcarbamate Triethylamine (0.259 mL, 1.86 mmol) was added to a solution of tert-butyl (3R,6S)-6-(2,3-difluorophenyl)-2-hydrazonoazepan-3-ylcarbamate from Step A (548 mg, 1.55 mmol), 3,3,3-trifluoropropionic acid (0.205 mL, 2.32 mmol), EDC (356 mg, 1.86 mmol), and 1-hydroxy-7-azabenzotriazole (253 mg, 1.86 mmol) in dichloromethane (55 mL). After 18 h, saturated aqueous NaHCO$_3$ was added and the mixture was extracted with CH$_2$Cl$_2$ (3×). The combined organic extracts were dried over Na$_2$SO$_4$, filtered, and concentrated under reduced pressure. The residue was purified by silica gel chromatography, eluting with a gradient of CH$_2$Cl$_2$:MeOH—100:0 to 96:4, to give the title compound. MS: m/z=447 (M+1).

INTERMEDIATES 14-15

Essentially following the procedures outlined for Intermediate 13, the compounds listed in Table 2 were prepared. The requisite starting materials were commercially available, described in the literature, synthesized according to methodology described herein, or readily synthesized by one skilled in the art of organic synthesis.

TABLE 2

| Intermediate | R | MS (M + 1) |
|---|---|---|
| 14 | ![F$_3$C group] | 473 |
| 15 | ![HO group] | 423 |

EXAMPLE 1

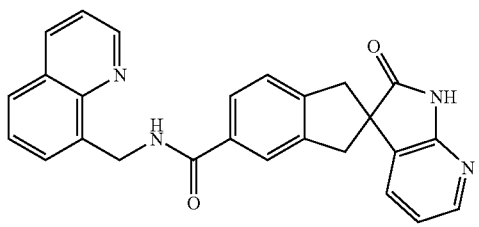

(±)-2'-Oxo-N-(quinolin-8-ylmethyl)-1,1',2',3-tetrahydrospiro[indene-2,3'-pyrrolo[2,3-b]pyridine]-5-carboxamide A mixture of 8-(aminomethyl)quinoline (41 mg, 0.177 mmol), (A)-2'-oxo-1,1',2',3-tetrahydrospiro[indene-2,3'-pyrrolo[2,3-h]pyridine]-5-carboxylic acid (described in Intermediate 2) (50 mg, 0.177 mmol), EDC (34 mg, 0.177 mmol), HOBT (27 mg, 0.177 mmol), and N,N-diisopropylethylamine (0.093 mL, 0.532 mmol) was stirred in DMF (2 mL) at ambient temperature for 18 h. The crude mixture was purified directly by HPLC using a reversed phase C18 column and eluting with a gradient of $H_2O:CH_3CN:CF_3CO_2H$—90:10:0.1 to 5:95:0.1. Lyophilization provided the title compound. MS: m/z=421 (M+1). HRMS: m/z=421.1669; calculated m/z=421.1659 for $C_{26}H_{21}N_4O_2$.

EXAMPLES 2-27

Essentially following the procedures outlined for Example 1, the compounds listed in Table 3 were prepared. The requisite amines were commercially available, described in the literature, synthesized according to methodology described herein (vide supra), or readily synthesized by one skilled in the art of organic synthesis. In some cases, straightforward protecting group strategies were applied.

TABLE 3

| Example | R$^a$ | MS (M + 1) |
|---|---|---|
| 2 | benzyl-piperidin-4-ylamine | 453 |
| 3 | 5-phenylpyridin-3-ylamine | 433 |
| 4 | trifluoroethyl-benzazepinone-amine | 521 |
| 5 | trifluoroethyl-benzoxazepinone-amine | 523 |
| 6 | 2-(4-phenylpiperidin-1-yl)ethylamine | 467 |
| 7 | 3-methyl-1-(4-aminophenyl)imidazolidin-2-one | 454 |
| 8 | 1-methyl-6-(2,3-difluorophenyl)-azepan-2-one-amine | 517 |
| 9 | 1-trifluoroethyl-6-(2,3-difluorophenyl)-azepan-2-one-amine | 585 |

TABLE 3-continued

| Example | R$^a$ | MS (M + 1) |
|---|---|---|
| 10 | 2-hydroxy-2-methylpropyl / (7S)-7-amino-5-(2,3-difluorophenyl)azepan-2-one derivative | 575 |
| 11 | (2-oxoindolin-3-yl)methylamine | 425 |
| 12 | (1-phenyl-1H-benzimidazol-2-yl)methylamine | 486 |
| 13 | 2-(3,4-dihydroisoquinolin-2(1H)-yl)ethylamine | 439 |
| 14 | 2-(3-(o-tolyl)pyrrolidin-1-yl)ethylamine | 467 |
| 15 | 2-(4-benzylpiperidin-1-yl)ethylamine | 481 |
| 16 | 2-oxo-1,2,3,4-tetrahydroquinolin-4-amine | 425 |
| 17 | isoquinolin-1-amine | 407 |
| 18 | isoquinolin-8-ylmethylamine | 421 |
| 19 | 1-(benzylsulfonyl)piperidin-4-amine | 517 |
| 20 | 1-(2-(2,3-difluorophenyl)ethyl)piperidin-4-amine | 503 |
| 21 | (3R)-1-phenethylpyrrolidin-3-amine | 453 |
| 22 | (3S)-1-phenethylpyrrolidin-3-amine | 453 |
| 23 | 2-oxoindolin-6-amine | 411 |
| 24 | 2-(1H-indol-4-yl)ethylamine | 423 |

TABLE 3-continued

| Example | R$^a$ | MS (M + 1) |
|---|---|---|
| 25 | 5-indolyl-NH- | 395 |
| 26 | 3,5-bis(trifluoromethyl)benzyl-NH- | 506 |
| 27 | 4-sulfamoylbenzyl-NH- | 449 |

EXAMPLE 28

N-{(6S,9R)-6-(2,3-Difluorophenyl)-3-[1-(trifluoromethyl)cyclopropyl]-6,7,8,9-tetrahydro-5H-imidazo[1,2-a]azepin-9-yl}-2'-oxo-1,1',2',3-tetrahydrospiro[indene-2,3'-pyrrolo[2,3-b]pyridine]-5-carboxamide Step A: (6S,9R)-6-(2,3-Difluorophenyl)-3-[1-(trifluoromethyl)cyclopropyl]-6,7,8,9-tetrahydro-5H-imidazo[1,2-a]azepin-9-amine Trifluoroacetic acid (2 mL) was added to a solution of tert-butyl {(6S,9R)-6-(2,3-difluorophenyl)-3-[1-(trifluoromethyl)cyclopropyl]-6,7,8,9-tetrahydro-5H-imidazo[1,2-a]azepin-9-yl}carbamate (170 mg, 0.361 mmol, described in Intermediate 8) in CH$_2$Cl$_2$ (2 mL). After 1 h, saturated NaHCO$_3$ was added and the mixture was extracted with dichloromethane (3×). The combined organic extracts were washed with saturated brine, dried over MgSO$_4$, filtered and concentrated in vacuo to give the title compound. MS: m/z=372 (M+1).

Step B: N-{(6S,9R)-6-(2,3-Difluorophenyl)-3-[1-(trifluoromethyl)cyclopropyl]-6,7,8,9-tetrahydro-5H-imidazo[1,2-a]azepin-9-yl}-2'-oxo-1,1',2',3-tetrahydrospiro[indene-2,3'-pyrrolo[2,3-b]pyridine]-5-carboxamide Triethylamine (18.0 µL, 0.129 mmol), EDC (17 mg, 0.086 mmol), and HOBT (7.0 mg, 0.043 mmol) were added to a solution of (6S,9R)-6-(2,3-difluorophenyl)-3-[1-(trifluoromethyl)cyclopropyl]-6,7,8,9-tetrahydro-5H-imidazo[1,2-a]azepin-9-amine from Step A (16 mg, 0.043 mmol) and the hydrochloride salt of (±)-2'-oxo-1,1',2',3-tetrahydrospiro[indene-2,3'-pyrrolo[2,3-b]pyridine]-5-carboxylic acid (14.0 mg, 0.043 mmol, described in Intermediate 2) in N,N-dimethylformamide (1 mL). After 18 h, the reaction mixture was filtered and purified by HPLC using a reversed phase C18 column and eluting with a gradient of H$_2$O:CH$_3$CN:CF$_3$CO$_2$H—95:5:0.1 to 5:95:0.1. Lyophilization provided the title compound. MS: m/z=634 (M+1). HRMS: m/z=634.2265; calculated m/z=634.2236 for C$_{34}$H$_{29}$F$_5$N$_5$O$_2$.

EXAMPLES 29-32

Essentially following the procedures outlined for Example 28, the compounds listed in Table 4 were prepared. The requisite starting materials were commercially available, described in the literature, synthesized according to methodology described herein, or readily synthesized by one skilled in the art of organic synthesis.

TABLE 4

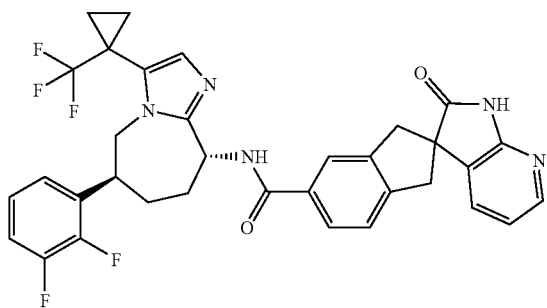

| Example | R$^1$ | MS (M + 1) |
|---|---|---|
| 29 | tert-butyl | 554 |
| 30 | methoxy-dimethyl | 598 |
| 31 | hydroxy-dimethyl | 584 |

TABLE 4-continued

| Example | R¹ | MS (M + 1) |
|---|---|---|
| 32 | HO~~~O~~~ (structure) | 628 |

EXAMPLE 33

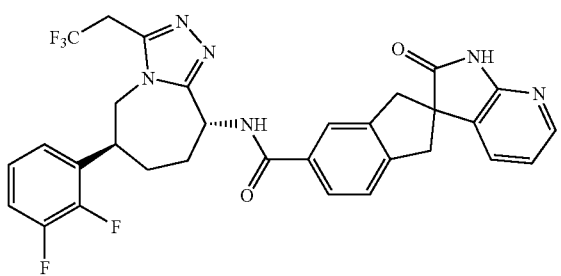

N-[(6S,9R)-6-(2,3-Difluorophenyl)-3-(2,2,2-trifluoroethyl)-6,7,8,9-tetrahydro-5H-[1,2,4]triazolo[4,3-a]azepin-9-yl]-2'-oxo-1,1',2',3-tetrahydrospiro[indene-2,3'-pyrrolo[2,3-b]pyridine]-5-carboxamide Step A: (6S,9R)-6-(2,3-Difluorophenyl)-3-(2,2,2-trifluoroethyl)-6,7,8,9-tetrahydro-5H-[1,2,4]triazolo[4,3-a]azepin-9-amine Hydrochloric acid (4.0 M in dioxane; 10 mL, 40.1 mmol) was added to a solution of tert-butyl [(6S,9R)-6-(2,3-difluorophenyl)-3-(2,2,2-trifluoroethyl)-6,7,8,9-tetrahydro-5H-[1,2,4]triazolo[4,3-a]azepin-9-yl]carbamate (618 mg, 1.384 mmol, described in Intermediate 13) in 1,4-dioxane (5 mL). After 1 h, the reaction was concentrated in vacuo to give the title compound as a bis hydrochloride salt. MS: m/z=347 (M+1).

Step B: N-[(6S,9R)-6-(2,3-Difluorophenyl-3-(2,2,2-trifluoroethyl)-6,7,8,9-tetrahydro-5H-[1,2,4]triazolo[4,3-a]azepin-9-yl]-2'-oxo-1,1',2',3-tetrahydrospiro[indene-2,3'-pyrrolo[2,3-b]pyridine]-5-carboxamide Triethylamine (58 µL, 0.417 mmol), EDC (27 mg, 0.143 mmol), and HOBT (16 mg, 0.119 mmol) were added to a solution of hydrochloride salt of (6S,9R)-6-(2,3-difluorophenyl)-3-(2,2,2-trifluoroethyl)-6,7,8,9-tetrahydro-5H-[1,2,4]triazolo[4,3-a]azepin-9-amine from Step A (50 mg, 0.119 mmol) and sodium salt of (±)-2'-oxo-1,1',2',3-tetrahydrospiro[indene-2,3'-pyrrolo[2,3-b]pyridine]-5-carboxylic acid (57 mg, 0.168 mmol, described in Intermediate 2) in N,N-dimethylformamide (2 mL). After 16 h, the mixture was diluted with EtOAc and sodium hydroxide (1 N in water). The mixture was extracted with EtOAc, washed with sodium hydroxide (2×), brine, dried over MgSO$_4$, filtered and concentrated in vacuo. The residue was purified by silica gel chromatography, eluting with a gradient of CH$_2$Cl$_2$:MeOH:NT$_4$OH—100:0:0 to 92:8:0.8, to give the title compound. MS: m/z=609 (M+1).

HRMS: m/z=609.1988; calculated m/z=609.2032 for C$_{31}$H$_{26}$F$_5$N$_6$O$_2$.

EXAMPLES 34-35

Essentially following the procedures outlined for Example 33, the compounds listed in Table 5 were prepared. The requisite starting materials were commercially available, described in the literature, synthesized according to methodology described herein, or readily synthesized by one skilled in the art of organic synthesis.

TABLE 5

| Example | R¹ | MS (M + 1) |
|---|---|---|
| 34 | F₃C-cyclopropyl (structure) | 635 |
| 35 | HO-C(CH₃)₂- (structure) | 585 |

EXAMPLES 36-62

Essentially following the procedures outlined for Example 1, but using Intermediate 3 in place of Intermediate 2, the compounds listed in Table 6 are prepared. The requisite amines are commercially available, described in the literature, synthesized according to methodology described herein (vide supra), or readily synthesized by one skilled in the art of organic synthesis. In some cases, straightforward protecting group strategies are applied.

TABLE 6
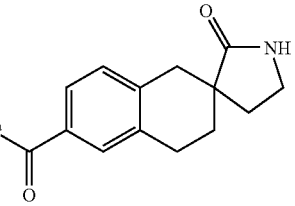
| Example | Rᵃ |
|---|---|
| 36 | 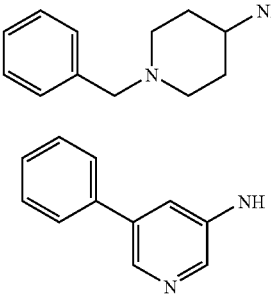 |
| 37 |  |
| 38 | 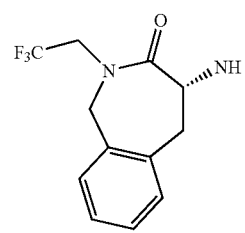 |
| 39 | 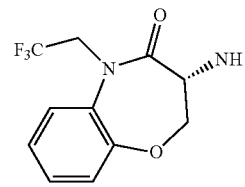 |
| 40 | 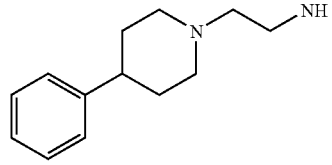 |
| 41 | 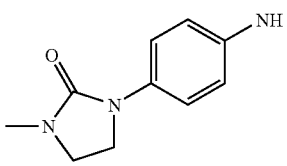 |
| 42 | 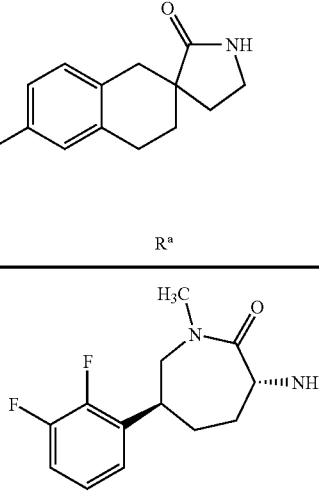 |
TABLE 6-continued
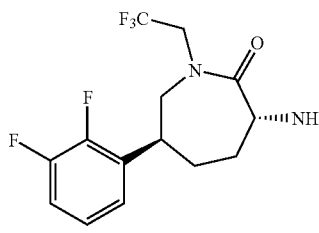
| Example | Rᵃ |
|---|---|
| 43 | 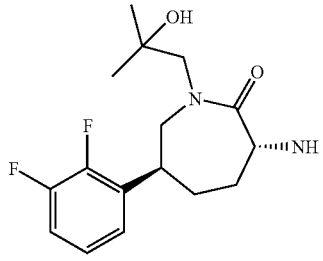 |
| 44 | 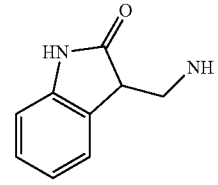 |
| 45 | 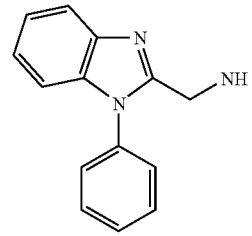 |
| 46 | 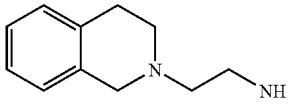 |
| 47 | |
| 48 | |

TABLE 6-continued

| Example | Rᵃ |
|---|---|
| 49 | 2-methylphenyl-pyrrolidin-3-yl, N-(2-aminoethyl) |
| 50 | 4-benzylpiperidin-1-yl, N-(2-aminoethyl) |
| 51 | 3,4-dihydroquinolin-2(1H)-one-4-yl amine |
| 52 | isoquinolin-1-yl amine |
| 53 | isoquinolin-8-ylmethyl amine |
| 54 | 1-(benzylsulfonyl)piperidin-4-yl amine |
| 55 | 2-(2,3-difluorophenyl)ethyl-piperidin-4-yl amine |
| 56 | (R)-1-(2-phenylethyl)pyrrolidin-3-yl amine |

TABLE 6-continued

| Example | Rᵃ |
|---|---|
| 57 | (S)-1-(2-phenylethyl)pyrrolidin-3-yl amine |
| 58 | 5-amino-2-oxindole |
| 59 | tryptamine |
| 60 | 5-aminoindole |
| 61 | 3,5-bis(trifluoromethyl)benzylamine |
| 62 | 4-(aminomethyl)benzenesulfonamide |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to an depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of formula I:

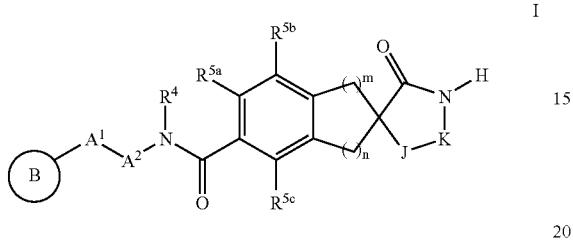

wherein:

B is a selected from the group consisting of: $C_{3-10}$cycloalkyl, phenyl, naphthyl, tetrahydronaphthyl, indanyl, biphenyl, phenanthryl, anthryl, azepanyl, azetidinyl, benzimidazolyl, benzisoxazolyl, benzofuranyl, benzofurazanyl, benzopyranyl, benzothiopyranyl, benzofuryl, benzothiazolyl, benzothienyl, benzoxazolyl, benzopyrazolyl, benzotriazolyl, chromanyl, cinnolinyl, dibenzofuranyl, dihydrobenzofuryl, dihydrobenzothienyl, dihydrobenzothiopyranyl, dihydrobenzothiopyranyl sulfone, furyl, furanyl, imidazolidinyl, imidazolinyl, imidazolyl, indolinyl, indolyl, isochromanyl, isoindolinyl, isoquinolinyl, isothiazolidinyl, isothiazolyl, morpholinyl, naphthyridinyl, oxazepanyl, oxadiazolyl, 2-oxoazepinyl, 4-oxonaphthyridinyl, 2-oxopiperazinyl, 2-oxopiperidinyl, 2-oxopyrrolidinyl, 2-oxopyridinyl, 2-oxoquinolinyl, 2-oxobenzimidazolyl, piperidinyl, piperazinyl, pyrazinyl, pyrazolidinyl, pyrazolyl, pyridazinyl, pyridinyl, pyridinyl, pyrimidinyl, pyrimidyl, pyrrolidinyl, pyrrolyl, quinazolinyl, quinolinyl, quinoxalinyl, tetrahydrofuranyl, tetrahydrofuryl, tetrahydroimidazopyridinyl, tetrahydroisoquinolinyl, tetrahydroquinolinyl, tetrazolyl, thiamorpholinyl, thiamorpholinyl sulfoxide, thiazepinyl, thiazolyl, thiazolinyl, thiazolidinyl, thienyl, and triazolyl, where B is unsubstituted or substituted with 1-5 substituents each independently selected from $R^1$, $R^2$, $R^{3a}$ and $R^{3b}$, $R^1$, $R^2$, $R^{3a}$ and $R^{3b}$ are independently selected from:

(1) —$C_{1-6}$alkyl, which is unsubstituted or substituted with 1-7 substituents each independently selected from:
  (a) halo,
  (b) hydroxy,
  (c) —O—$C_{1-6}$alkyl,
  (d) —$C_{3-6}$cycloalkyl,
  (e) phenyl or heterocycle, wherein heterocycle is selected from: pyridinyl, pyrimidinyl, pyrazinyl, pyridazinyl, piperidinyl, piperazinyl, pyrrolidinyl, thienyl and morpholinyl,
    which phenyl or heterocycle is unsubstituted or substituted with 1-5 substituents each independently selected from: —$C_{1-6}$alkyl, —O—$C_{1-6}$alkyl, halo, hydroxy, trifluoromethyl and —OCF$_3$, (f) —CO$_2$R$^9$, wherein R$^9$ is selected from: hydrogen, —$C_{1-6}$alkyl which is unsubstituted or substituted with 1-6 fluoro, —$C_{5-6}$cycloalkyl, benzyl and phenyl,
  (g) —NR$^{10}$R$^{11}$, wherein R$^{10}$ and R$^{11}$ are each independently selected from: hydrogen, —$C_{1-6}$alkyl which is unsubstituted or substituted with 1-6 fluoro, —$C_{5-6}$cycloalkyl, benzyl, phenyl, —COR$^9$ and —SO$_2$R$^{12}$,
  (h) —SO$_2$R$^{12}$, wherein R$^{12}$ is selected from: —$C_{1-6}$alkyl which is unsubstituted or substituted with 1-6 fluoro, —$C_{5-6}$cycloalkyl, benzyl and phenyl,
  (i) CONR$^{10a}$R$^{11a}$, wherein R$^{10a}$ and R$^{11a}$ are each independently selected from:
    hydrogen, —$C_{1-6}$alkyl which is unsubstituted or substituted with 1-6 fluoro, —$C_{5-6}$cycloalkyl, benzyl and phenyl,
    or R$^{10a}$ and R$^{11a}$ are joined to form a ring selected from azetidinyl, pyrrolidinyl, piperidinyl, piperazinyl and morpholinyl, which ring is unsubstituted or substituted with 1-5 substituents each independently selected from: —$C_{1-6}$alkyl, —O—$C_{1-6}$alkyl, halo, hydroxyl, phenyl and benzyl,
  (j) trifluoromethyl,
  (k) —OCO$_2$R$^9$,
  (l) —(NR$^{10a}$)CO$_2$R$^9$,
  (m) —O(CO)NR$^{10a}$R$^{11a}$, and
  (n) —(NR$^9$)(CO)NR$^{10a}$R$^{11a}$, (2) —$C_{3-6}$cycloalkyl, which is unsubstituted or substituted with 1-7 substituents each independently selected from: halo, hydroxy, —O—$C_{1-6}$alkyl, trifluoromethyl and phenyl, which phenyl is unsubstituted or substituted with 1-5 substituents each independently selected from: —$C_{1-6}$alkyl, —O—$C_{1-6}$alkyl, halo, hydroxy and trifluoromethyl, (3) phenyl or heterocycle, wherein heterocycle is selected from: pyridinyl, pyrimidinyl, pyrazinyl, thienyl, pyridazinyl, pyrrolidinyl, azetidinyl, thiazolyl, isothiazolyl, oxazolyl, isoxazolyl, imidazolyl, triazolyl, tetrazolyl, azepanyl, benzimidazolyl, benzopyranyl, benzofuryl, benzothiazolyl, benzoxazolyl, chromanyl, furyl, imidazolidinyl, imidazolinyl, indolinyl, indolyl, quinolinyl, isoquinolinyl, tetrahydroquinolinyl, isoindolinyl, tetrahydroisoquinolinyl, 2-oxopiperazinyl, 2-oxopiperidinyl, 2-oxopyrrolidinyl, pyrazolidinyl, pyrazolyl, pyrrolyl, quinazolinyl, tetrahydrofuryl, thiazolinyl, purinyl, naphthyridinyl, quinoxalinyl, quinazolinyl, 1,3-dioxolanyl, oxadiazolyl, piperidinyl and morpholinyl, which phenyl or heterocycle is unsubstituted or substituted with 1-5 substituents each independently selected from:
  (a) —$C_{1-6}$alkyl which is unsubstituted or substituted with 1-6 fluoro,
  (b) halo,
  (c) hydroxy,
  (d) —O—$C_{1-6}$alkyl, which is unsubstituted or substituted with 1-6 fluoro,
  (e) —$C_{3-6}$cycloalkyl,
  (f) phenyl or heterocycle, wherein heterocycle is selected from: pyridinyl, pyrimidinyl, pyrazinyl, thienyl and morpholinyl,
    which phenyl or heterocycle is unsubstituted or substituted with 1-5 substituents each independently selected from: —$C_{1-6}$alkyl, —O—$C_{1-6}$alkyl, halo, hydroxy and trifluoromethyl,
- (g) —$CO_2R^9$,
- (h) —$NR^{10}R^{11}$,
- (i) —$CONR^{10}R^{11}$,
- (j) —$SO_2R^{12}$, and
- (k) oxo,
- (4) halo,
- (5) oxo,
- (6) hydroxy,
- (7) —O—$C_{1-6}$alkyl, which is unsubstituted or substituted with 1-5 halo,
- (8) —CN,
- (9) —$CO_2R^9$,
- (10) —$NR^{10}R^{11}$,
- (11) —$SO_2R^{12}$,
- (12) —$CONR^{10a}R^{11a}$,
- (13) —$OCO_2R^9$,
- (14) —$(NR^{10a})CO_2R^9$,
- (15) —$O(CO)NR^{10a}R^{11a}$,
- (16) —$(NR^9)(CO)NR^{10a}R^{11a}$,
- (17) —$SO_2NR^{10a}R^{11a}$,
- (18) —$SR^{12}$,
- (19) —$S(O)R^{12}$,
- (20) —$(NR^9)(CO)NR^{10a}R^{11a}$
- (21) —(CO)—$(CO)NR^{10a}R^{11a}$, and
- (22) —(CO)—$(CO)OR^9$;

or $R^{3a}$ and $R^{3b}$ and the atom(s) to which they are attached are joined to form a ring selected from cyclobutyl, cyclopentenyl, cyclopentyl, cyclohexenyl, cyclohexyl, phenyl, naphthyl, thienyl, thiazolyl, thiazolinyl, oxazolyl, oxazolinyl, imidazolyl, imidazolinyl, imidazolidinyl, thiadiazolyl, oxadiazolyl, isoxazolyl, pyrazolyl, triazolyl, pyridinyl, pyrimidyl, pyrazinyl, pyridazinyl, triazinyl, pyrrolyl, pyrrolinyl, morpholinyl, azetidinyl, pyrrolidinyl, piperidinyl, tetrahydrofuranyl, tetrahydropyranyl, tetrahydropyridinyl, furanyl, dihydrofuranyl, dihydropyranyl and piperazinyl, which ring is unsubstituted or substituted with 1-5 substituents each independently selected from:
- (a) —$C_{1-6}$alkyl, which is unsubstituted or substituted with 1-3 substituents each independently selected from:
  - (i) halo,
  - (ii) hydroxy,
  - (iii) —O—$C_{1-6}$alkyl, which is unsubstituted or substituted with 1-5 substituents each independently selected from: —O—$C_{1-6}$alkyl, halo, and hydroxy, (iv)
  - —$C_{3-6}$cycloalkyl, which is unsubstituted or substituted with 1-5 substituents each independently selected from: —$C_{1-6}$alkyl, —O—$C_{1-6}$alkyl, halo, hydroxy, trifluoromethyl and —$OCF_3$, (v) phenyl or heterocycle, wherein heterocycle is selected from: pyridinyl, pyrimidinyl, pyrazinyl, pyridazinyl, piperidinyl, piperazinyl, pyrrolidinyl, thienyl and morpholinyl, which phenyl or heterocycle is unsubstituted or substituted with 1-5 substituents each independently selected from: —$C_{1-6}$alkyl, —O—$C_{1-6}$alkyl, halo, hydroxy, trifluoromethyl and —$OCF_3$,
  - (vi) —$CO_2R^9$,
  - (vii) —$NR^{10}R^{11}$,
  - (viii) —$SO_2R^{12}$,
  - (ix) —$CONR^{10a}R^{11a}$, and
  - (x) —$(NR^{10a})CO_2R^9$,
- (b) —$C_{3-6}$cycloalkyl, which is unsubstituted or substituted with 1-5 substituents each independently selected from: halo, hydroxy, —O—$C_{1-6}$alkyl, trifluoromethyl and phenyl,
- (c) phenyl or heterocycle, wherein heterocycle is selected from: pyridinyl, pyrimidinyl, pyrazinyl, thienyl, pyridazinyl, pyrrolidinyl, azetidinyl, piperidinyl and morpholinyl, which phenyl or heterocycle is unsubstituted or substituted with 1-3 substituents each independently selected from: halo, hydroxy, —$C_{3-6}$cycloalkyl, —O—$C_{1-6}$alkyl which is unsubstituted or substituted with 1-6 fluoro, and —$C_{1-6}$alkyl which is unsubstituted or substituted with 1-6 fluoro,
- (d) halo,
- (e) —$SO_2R^{12}$,
- (f) hydroxy,
- (g) —O—$C_{1-6}$alkyl which is unsubstituted or substituted with 1-5 halo,
- (h) —CN,
- (i) —$COR^{12}$,
- (j) —$NR^{10}R^{11}$,
- (k) —$CONR^{10a}R^{11a}$,
- (l) —$CO_2R^9$,
- (m) —$(NR^{10a})CO_2R^9$,
- (n) —$O(CO)NR^{10a}R^{11a}$,
- (o) —$(NR^9)(CO)NR^{10a}R^{11a}$, and
- (p) oxo;

$A^1$ and $A^2$ are each independently selected from:
- (1) a bond,
- (2) —$CR^{13}R^{14}$—, wherein $R^{13}$ and $R^{14}$ are independently selected from:
  - (a) hydrogen,
  - (b) $C_{1-6}$ alkyl, which is unsubstituted or substituted with 1-5 substituents each independently selected from: halo, hydroxy, —$NR^{10}R^{11}$, —$CONR^{10a}R^{11a}$ and —$CO_2R^9$,
  - (c) phenyl, which is unsubstituted or substituted with 1-3 substituents each independently selected from: $C_{1-4}$alkyl, hydroxyl and halo,
  - (d) —$CONR^{10}$—$(C_{1-6}$alkyl)-$NR^{15}R^{16}$, wherein $R^{15}$ and $R^{16}$ are each independently selected from: hydrogen, —$C_{1-6}$alkyl, —$COR^9$ and —$CO_2R^9$,
  - (e) —$CO_2R^9$,
  - (f) —$CONR^{10a}R^{11a}$, and
  - (g) hydroxy, and
- (3) —$CH_2CR^{13}R^{14}$—, wherein one of $A^1$ and $A^2$ is optionally absent;

J is selected from: =$C(R^{6a})$—, —$CR^{13}R^{14}$— and —C(=O)—;

K is selected from: =$C(R^{6b})$—, —$CR^{13}R^{14}$—, —C(=O)—, —$SO_2$—, =N— and —$N(R^{6b})$—;

$R^4$ is selected from: hydrogen, $C_{1-6}$ alkyl which is unsubstituted or substituted with 1-6 fluoro, $C_{5-6}$ cycloalkyl, benzyl and phenyl, or $R^4$ is joined to B to form a ring selected from piperidinyl, pyrrolidinyl, piperazinyl, azetidinyl, azepinyl and morpholinyl, which ring is unsubstituted or substituted with 1-5 substituents each independently selected from: —$C_{1-6}$alkyl, —O—$C_{1-6}$alkyl, halo, hydroxy, phenyl and benzyl;

$R^{5a}$, $R^{5b}$ and $R^{5c}$ are each independently selected from: hydrogen, $C_{1-6}$ alkyl, —O—$C_{1-6}$alkyl, —$OCF_3$, trifluoromethyl, halo, hydroxy and —CN;

$R^{6a}$ and $R^{6b}$ are each independently selected from:
(1) hydrogen;
(2) —$C_{1-4}$alkyl, which is unsubstituted or substituted with 1-5 substituents each independently selected from:
(a) halo,
(b) —O—$C_{1-6}$alkyl,
(c) —$C_{3-6}$cycloalkyl,
(d) phenyl or heterocycle, wherein heterocycle is selected from: imidazolyl, oxazolyl, pyridinyl, pyrimidinyl, pyrazinyl, pyridazinyl, piperidinyl, piperazinyl, pyrrolidinyl, thiazolyl, thienyl, triazolyl, or morpholinyl, which phenyl or heterocycle is unsubstituted or substituted with 1-3 substituents each independently selected from: —$C_{1-6}$alkyl, —O—$C_{1-6}$alkyl, halo, hydroxy, trifluoromethyl and —$OCF_3$,
(4) phenyl or heterocycle, wherein heterocycle is selected from: pyridinyl, pyrimidinyl, pyrazinyl, thienyl, pyrrolidinyl, azetidinyl, thiazolyl, oxazolyl, imidazolyl, triazolyl, tetrahydrofuryl, piperidinyl, and morpholinyl, which phenyl or heterocycle is unsubstituted or substituted with 1-3 substituents each independently selected from: —$C_{1-4}$alkyl which is unsubstituted or substituted with 1-5 fluoro, halo, hydroxy, —O—$C_{1-4}$alkyl which is unsubstituted or substituted with 1-5 fluoro, —$C_{3-6}$cycloalkyl and phenyl,
(5) halo,
(6) hydroxy,
(7) —O—$C_{1-6}$alkyl, which is unsubstituted or substituted with 1-5 halo,
(8) —CN,
(9) —$CO_2R^9$,
(10) —$NR^{10}R^{11}$, and
(11) —$CONR^{10a}R^{11a}$,
or $R^{6a}$ and $R^{6b}$ and the atom(s) to which they are attached are joined to form a ring selected from cyclopentenyl, cyclohexenyl, phenyl, pyridinyl, pyrimidinyl, pyrazinyl, pyridazinyl, furanyl, dihydrofuranyl, dihydropyranyl, thiazolyl, isothiazolyl, oxazolyl, isoxazolyl, imidazolyl, triazolyl, thienyl, dihydrothienyl and dihydrothiopyranyl, which ring is unsubstituted or substituted with 1-5 substituents each independently selected from:
(a) —$C_{1-6}$alkyl, which is unsubstituted or substituted with 1-3 substituents each independently selected from:
(i) halo,
(ii) hydroxy,
(iii) —O—$C_{1-6}$alkyl,
(iv) —$C_{3-6}$cycloalkyl,
(v) phenyl or heterocycle, wherein heterocycle is selected from: pyridinyl, pyrimidinyl, pyrazinyl, pyridazinyl, piperidinyl, piperazinyl, pyrrolidinyl, thienyl, or morpholinyl, which is unsubstituted or substituted with 1-5 substituents where the substituents are each independently selected from: —$C_{1-6}$alkyl, —O—$C_{1-6}$alkyl, halo, hydroxy, trifluoromethyl and —$OCF_3$,
(vi) —$CO_2R^9$,
(vii) —$NR^{10}R^{11}$,
(viii) —$SO_2R^{12}$,
(ix) —$CONR^{10a}R^{11a}$, and
(x) —$(NR^{10a})CO_2R^9$,
(b) phenyl or heterocycle, wherein heterocycle is selected from: pyridinyl, pyrimidinyl, pyrazinyl, thienyl, pyridazinyl, pyrrolidinyl, azetidinyl, piperidinyl and morpholinyl, which phenyl or heterocycle is unsubstituted or substituted with 1-3 substituents each independently selected from:
—$C_{1-6}$alkyl, which is unsubstituted or substituted with 1-6 fluoro, —O—$C_{1-6}$alkyl, which is unsubstituted or substituted with 1-6 fluoro, halo, hydroxy, and —$C_{3-6}$cycloalkyl,
(c) halo,
(d) —$SO_2R^{12}$,
(e) hydroxy,
(f) —O—$C_{1-6}$alkyl, which is unsubstituted or substituted with 1-5 halo,
(g) —CN,
(h) —$COR^{12}$,
(i) —$NR^{10}R^{11}$,
(j) —$CONR^{10a}R^{11a}$,
(k) —$CO_2R^9$,
(l) —$(NR^{10a})CO_2R^9$,
(m) —$O(CO)NR^{10a}R^{11a}$,
(n) —$(NR^9)(CO)NR^{10a}R^{11a}$, and
(o) oxo;
m is 1 or 2;
n is 1 or 2;
a pharmaceutically acceptable salt or individual diastereoisomer thereof.

2. The compound of claim 1 having the formula Ia:

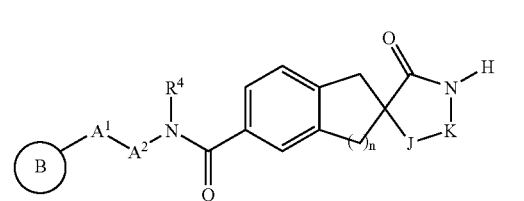

a pharmaceutically acceptable salt or individual diastereoisomer thereof.

3. The compound of claim 1 having the formula Ib:

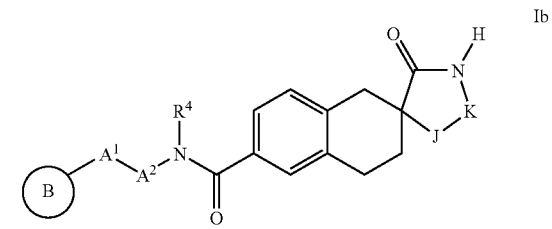

a pharmaceutically acceptable salt or individual diastereoisomer thereof.

4. The compound of claim 1 having the formula Ic:

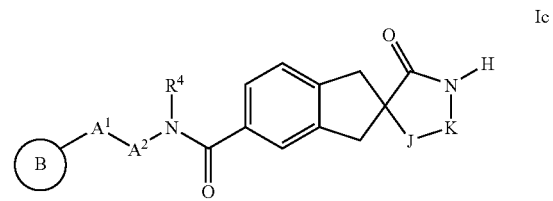

a pharmaceutically acceptable salt or individual diastereoisomer thereof.

5. The compound of claim 1 having the formula Id:

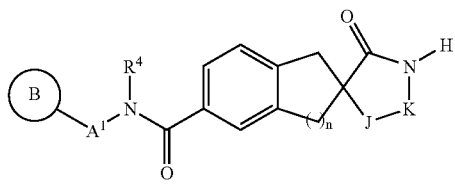

Id a pharmaceutically acceptable salt or individual diastereoisomer thereof.

6. The compound of claim 1 having the formula Ie:

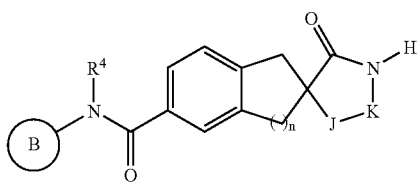

Ie a pharmaceutically acceptable salt or individual diastereoisomer thereof.

7. The compound of claim 1 having the formula If:

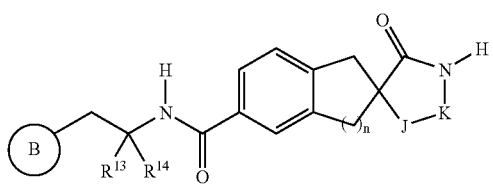

If a pharmaceutically acceptable salt or individual diastereoisomer thereof.

8. The compound of claim 1 having the formula Ig:

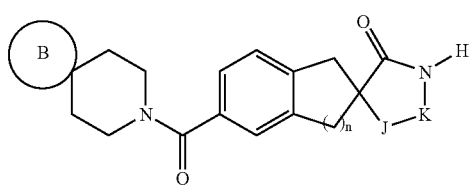

Ig a pharmaceutically acceptable salt or individual diastereoisomer thereof.

9. The compound of claim 1, wherein B is selected from the group consisting of: $C_{3-10}$cycloalkyl, phenyl, naphthyl, tetrahydronaphthyl, indanyl, biphenyl, azepanyl, benzimidazolyl, imidazolyl, imidazolinyl, imidazolidinyl, indolinyl, indolyl, isoquinolinyl, morpholinyl, naphthyridinyl, oxazepanyl, 2-oxoazepanyl, 2-oxooxazepanyl, 2-oxopyrrolidinyl, 2-oxopyridinyl, piperazinyl, piperidinyl, pyrazinyl, pyridinyl, pyrimidinyl, pyrrolidinyl, pyrolyl, quinazolinyl, quinolinyl, quinoxalinyl, tetrahydrofuranyl, tetrahydroisoquinolinyl, tetrahydroquinolinyl, thiazolyl, and thiazolinyl, where B is unsubstituted or substituted with 1-5 substituents each independently selected from $R^1$, $R^2$, $R^{3a}$ and $R^{3b}$.

10. The compound of claim 1, wherein $R^1$, $R^2$, $R^{3a}$ and $R^{3b}$ are independently selected from:

(1) —$C_{1-6}$alkyl, which is unsubstituted or substituted with 1-5 substituents each independently selected from:
  (a) halo,
  (b) hydroxy,
  (c) —O—$C_{1-6}$alkyl,
  (d) —$C_{3-6}$cycloalkyl,
  (e) phenyl or heterocycle, wherein heterocycle is selected from: pyridinyl, piperidinyl, piperazinyl, pyrrolidinyl, and morpholinyl,
    which phenyl or heterocycle is unsubstituted or substituted with 1-3 substituents each independently selected from: —$C_{1-6}$alkyl, —O—$C_{1-6}$alkyl, halo, hydroxy, trifluoromethyl and —$OCF_3$,
  (f) —$NR^{10}R^{11}$,
  (g) —$CONR^{10a}R^{11a}$, (2) —$C_{3-6}$cycloalkyl, which is unsubstituted or substituted with 1-5 substituents each independently selected from: halo, hydroxy, —O—$C_{1-6}$alkyl, trifluoromethyl and phenyl, (3) phenyl or heterocycle, wherein heterocycle is selected from: pyridinyl, pyrimidinyl, pyrazinyl, thienyl, pyrrolidinyl, oxazolyl, imidazolyl, triazolyl, tetrazolyl, imidazolidinyl, imidazolinyl, indolinyl, indolyl, quinolinyl, isoquinolinyl, tetrahydroquinolinyl, isoindolinyl, tetrahydroisoquinolinyl, 2-oxopiperazinyl, 2-oxopiperidinyl, 2-oxopyrrolidinyl, tetrahydrofuryl, 1,3-dioxolanyl, oxadiazolyl, piperidinyl and morpholinyl, which phenyl or heterocycle is unsubstituted or substituted with 1-3 substituents each independently selected from:
  (a) —$C_{1-6}$alkyl which is unsubstituted or substituted with 1-6 fluoro,
  (b) halo,
  (c) hydroxy,
  (d) —O—$C_{1-16}$alkyl, which is unsubstituted or substituted with 1-6 fluoro,
  (e) —$C_{3-6}$cycloalkyl,
  (f) phenyl, which is unsubstituted or substituted with 1-3 substituents each independently selected from: —$C_{1-6}$alkyl, —O—$C_{1-6}$alkyl, halo, hydroxy and trifluoromethyl,
  (g) —$NR^{10}R^{11}$, and
  (h) oxo, (4) halo,
(5) oxo,
(6) hydroxy,
(7) —O—$C_{1-6}$alkyl, which is unsubstituted or substituted with 1-5 halo,
(8) —CN,
(9) —$CO_2R^9$,
(10) —$NR^{10}R^{11}$,
(11) —$SO_2R^{12}$,
(12) —$CONR^{10a}R^{11a}$, and
(13) —$SO_2NR^{10a}R^{11a}$.

11. The compound of claim 1, wherein $R^1$, $R^2$, $R^{3a}$ and $R^{3b}$ are independently selected from:

(1) —$C_{1-6}$alkyl, which is unsubstituted or substituted with 1-5 substituents each independently selected from: halo, hydroxy, —$C_{3-6}$cycloalkyl and phenyl, which phenyl is unsubstituted or substituted with 1-3 substituents each independently selected from: —$C_{1-6}$alkyl, halo and trifluoromethyl,
(2) phenyl or heterocycle, wherein heterocycle is selected from: pyridinyl, pyrrolidinyl, piperidinyl, piperazinyl, imidazolinyl, imidazolidinyl and morpholinyl, which phenyl or heterocycle is unsubstituted or substituted with 1-3 substituents each independently selected from: —$C_{1-6}$alkyl which is unsubstituted or substituted with 1-6 fluoro, halo and oxo,
(3) halo,
(4) oxo,
(5) hydroxy,
(6) —O—$C_{1-16}$alkyl, which is unsubstituted or substituted with 1-5 halo,
(7) —CN,
(8) —$SO_2R^{12}$, and
(9) —$SO_2NR^{10a}R^{11a}$,
or $R^{3a}$ and $R^{3b}$ and the atom(s) to which they are attached are joined to form a ring selected from phenyl, thiazolinyl, triazoyl, imidazolyl, imidazolinyl, pyridinyl, moipholinyl, pyrrolidinyl, piperidinyl, and tetrahydrofuranyl, which ring is unsubstituted or substituted with 1-5 substituents each independently selected from:
(a) —$C_{1-6}$alkyl, which is unsubstituted or substituted with 1-3 substituents each independently selected from:
(i) halo,
(ii) hydroxy,
(v) —O—$C_{1-6}$alkyl, which is unsubstituted or substituted with 1-5 substituents each independently selected from: —O—$C_{1-6}$alkyl, halo, and hydroxy,
(vi) —$C_{3-6}$cycloalkyl, and
(b) —$C_{3-6}$cycloalkyl, which is unsubstituted or substituted with 1-3 substituents each independently selected from: halo, hydroxy, —O—$C_{1-6}$alkyl, trifluoromethyl and phenyl,
(c) phenyl or heterocycle, wherein heterocycle is selected from: pyridinyl, pyrrolidinyl, piperidinyl and morpholinyl, which phenyl or heterocycle is unsubstituted or substituted with 1-3 substituents each independently selected from: halo, hydroxy, —$C_{3-6}$cycloalkyl, —O—$C_{1-6}$alkyl, and —$C_{1-6}$alkyl,
(d) halo,
(f) hydroxy,
(g) —O—$C_{1-6}$alkyl which is unsubstituted or substituted with 1-5 halo,
(i) —$COR^{12}$,
(j) —$NR^{10}R^{11}$,
(k) —$CONR^{10a}R^{11a}$, and
(p) oxo.
12. The compound of claim 1, wherein $A^1$ is —$CH_2$— or a bond, and $A^2$ is —$CHR^{13}$— or a bond.
13. The compound of claim 1, wherein J is =$C(R^{6a})$— or —$CH_2$—.
14. The compound of claim 1, wherein K is selected from: =$C(R^{6b})$—, —$CH_2$— and —$C(=O)$—.
15. The compound of claim 1, wherein $R^4$ is hydrogen or —$C_{1-6}$alkyl which is unsubstituted or substituted with fluoro, or $R^4$ is joined to B to form a piperidinyl ring.
16. The compound of claim 1, wherein $R^{5a}$, $R^{5b}$ and $R^{5c}$ are each independently selected from hydrogen, $C_{1-6}$alkyl and halo.
17. The compound of claim 1, wherein $R^{6a}$ and $R^{6b}$ are each independently selected from:

(1) hydrogen;
(2) —$C_{1-4}$alkyl, which is unsubstituted or substituted with 1-3 substituents where the substituents are each independently selected from: halo, —O—$C_{1-16}$alkyl, —$C_{3-6}$cycloalkyl, and phenyl,
(3) phenyl or heterocycle, wherein heterocycle is selected from: pyridinyl, pyrimidinyl, pyrazinyl, thiazolyl, oxazolyl, tetrahydrofuryl, piperidinyl, and morpholinyl, which phenyl or heterocycle is unsubstituted or substituted with 1-3 substituents each independently selected from: halo, hydroxy, —$C_{1-4}$alkyl which is unsubstituted or substituted with 1-3 fluoro, and —O—$C_{1-4}$alkyl which is unsubstituted or substituted with 1-3 fluoro,
(4) halo,
(5) —$NR^{10}R^{11}$,
(6) hydroxy,
(7) —O—$C_{1-4}$alkyl, which is unsubstituted or substituted with 1-3 halo.
18. The compound of claim 1, wherein $R^{6a}$ and $R^{6b}$ and the atom(s) to which they are attached join to form a ring selected from phenyl, pyridinyl, pyrimidinyl, pyrazinyl, pyridazinyl, thiazolyl, oxazolyl, imidazolyl, thienyl, which ring is unsubstituted or substituted with 1-3 substituents each independently selected from:
(a) —$C_{1-4}$alkyl, which is unsubstituted or substituted with 1-3 substituents each independently selected from: halo, —O—$C_{1-6}$alkyl, —$CO_2R^9$, —$NR^{10}R^{11}$, —$CONR^{10a}R^{11a}$,
(b) phenyl or heterocycle, wherein heterocycle is selected from: pyridinyl, pyrimidinyl, pyrazinyl, pyrrolidinyl, azetidinyl, piperidinyl and morpholinyl, which phenyl or heterocycle is unsubstituted or substituted with 1-3 substituents each independently selected from: halo, hydroxyl, —$C_{1-4}$alkyl which is unsubstituted or substituted with 1-5 fluoro, and —O—$C_{1-4}$alkyl which is unsubstituted or substituted with 1-3 fluoro,
(c) halo,
(d) hydroxy,
(e) —O—$C_{1-6}$alkyl which is unsubstituted or substituted with 1-5 halo,
(f) —CN,
(g) —$NR^{10}R^{11}$,
(h) —$CONR^{10a}R^{11a}$, and
(i) oxo.
19. The compound of claim 1, wherein $R^{13}$ and $R^{14}$ are independently selected from:
(a) hydrogen,
(b) phenyl,
(c) —$CONR^{10}$—($C_{1-6}$alkyl)—$NR^{15}R^{16}$, wherein $R^{15}$ and $R^{16}$ are independently selected from: hydrogen, —$C_{1-6}$alkyl and —$CO_2R^9$, and
(d) —$CO_2R^9$.
20. A compound selected from:

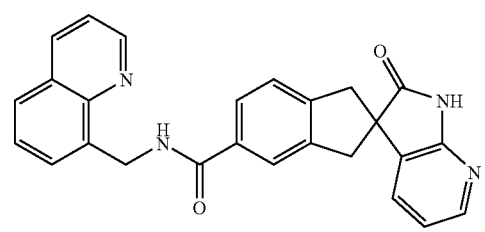

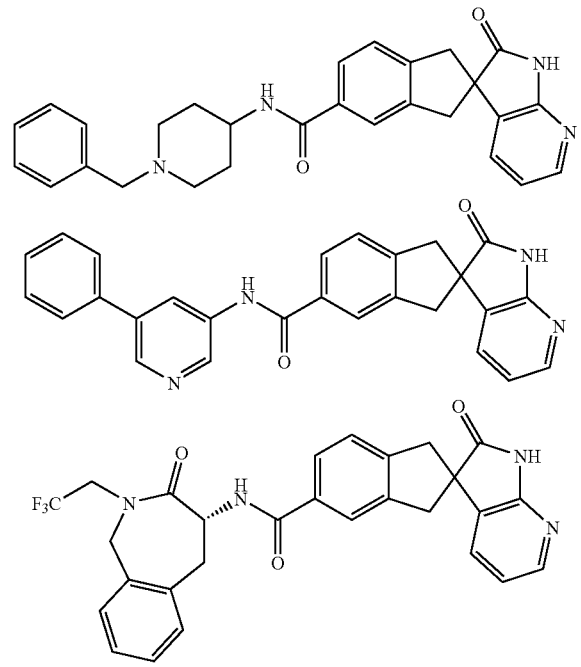
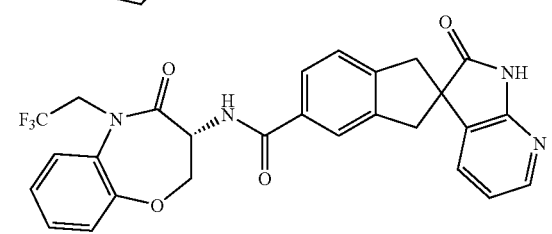
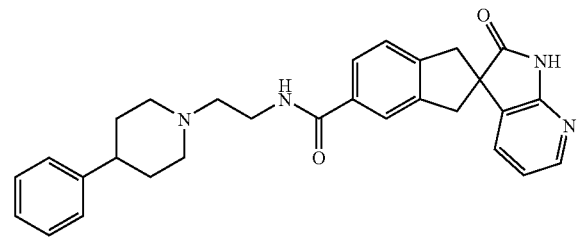
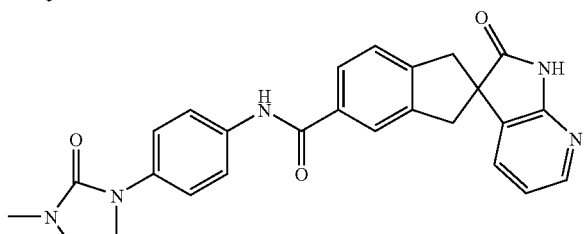
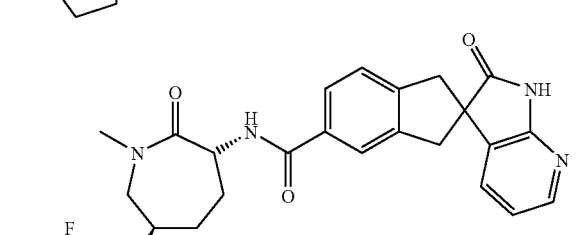
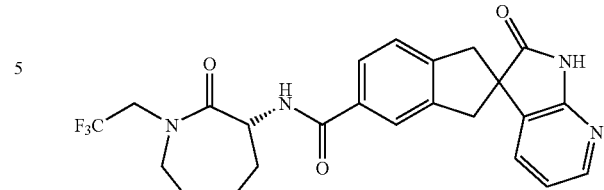
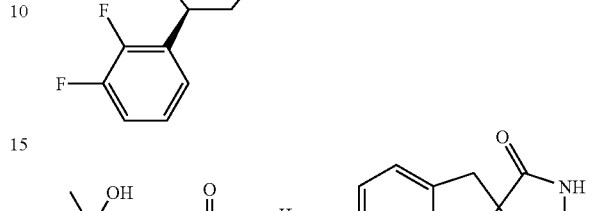
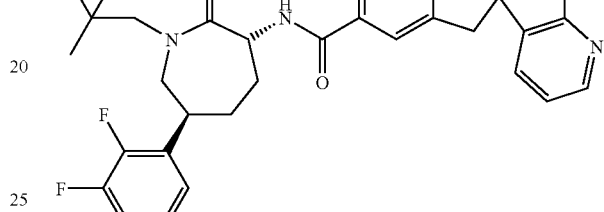
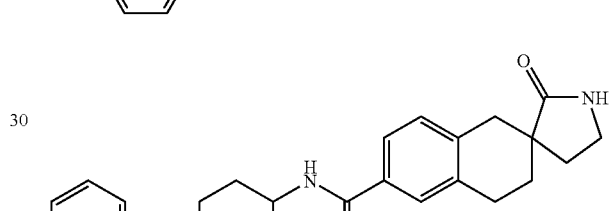
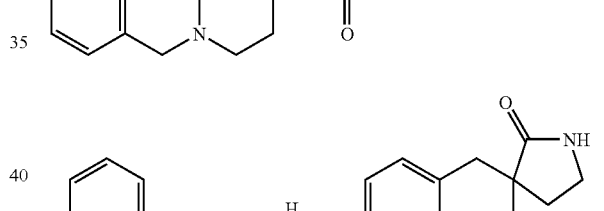
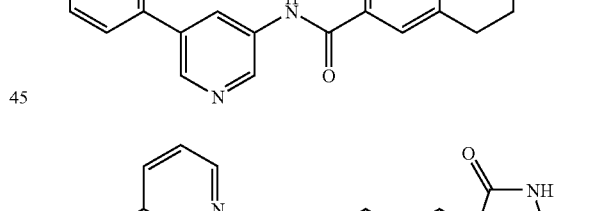
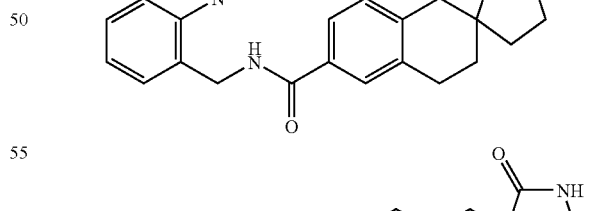
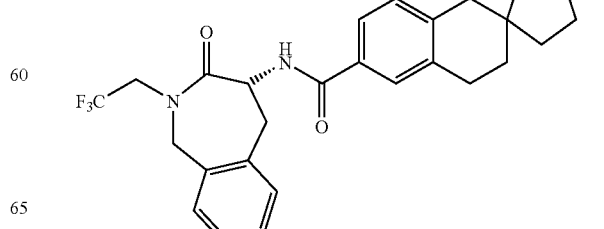

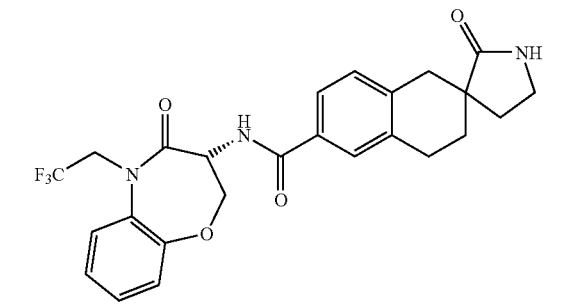
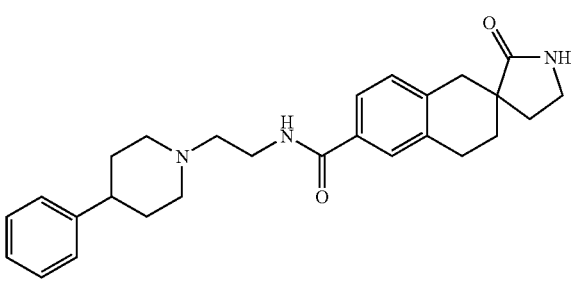
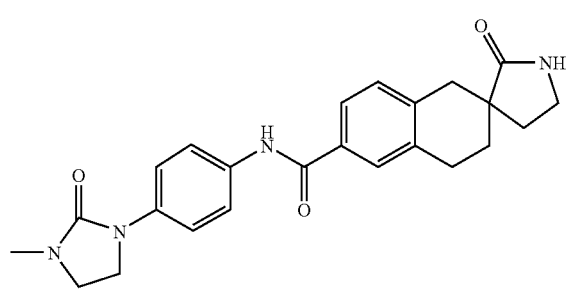
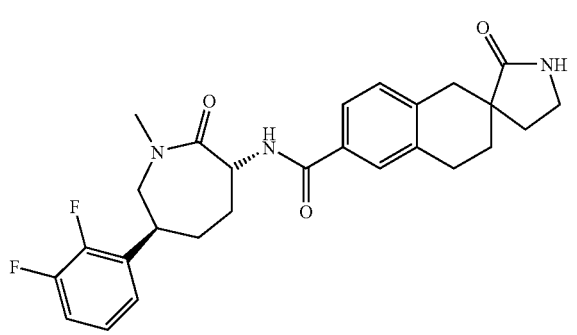
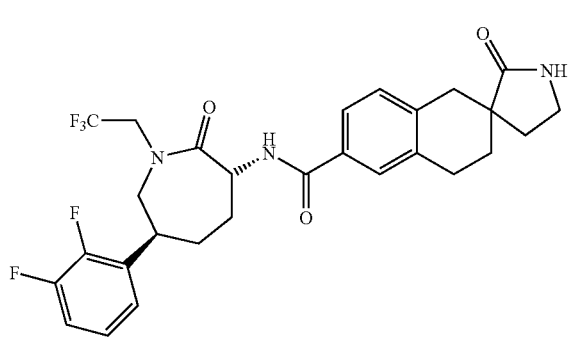
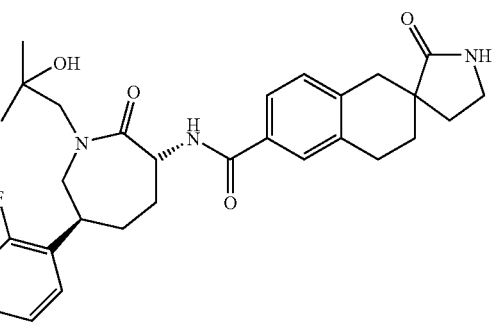
and pharmaceutically acceptable salts and individual diastereomers thereof.
21. A Compound selected from:
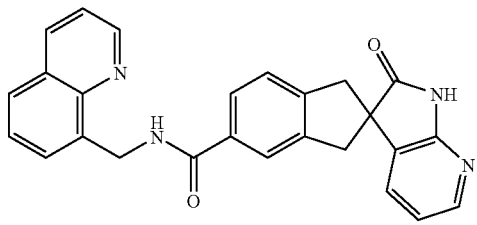
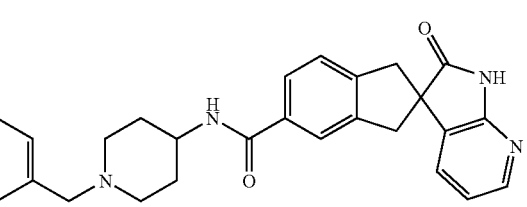
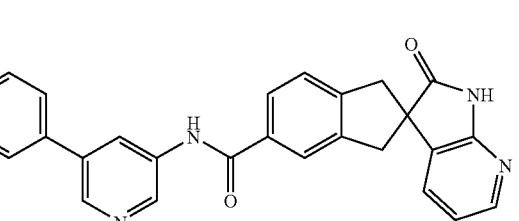
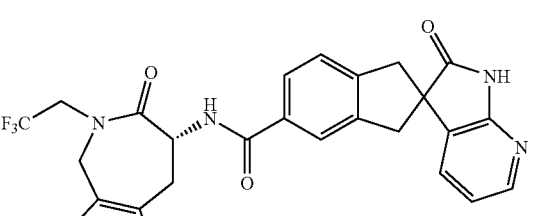

-continued
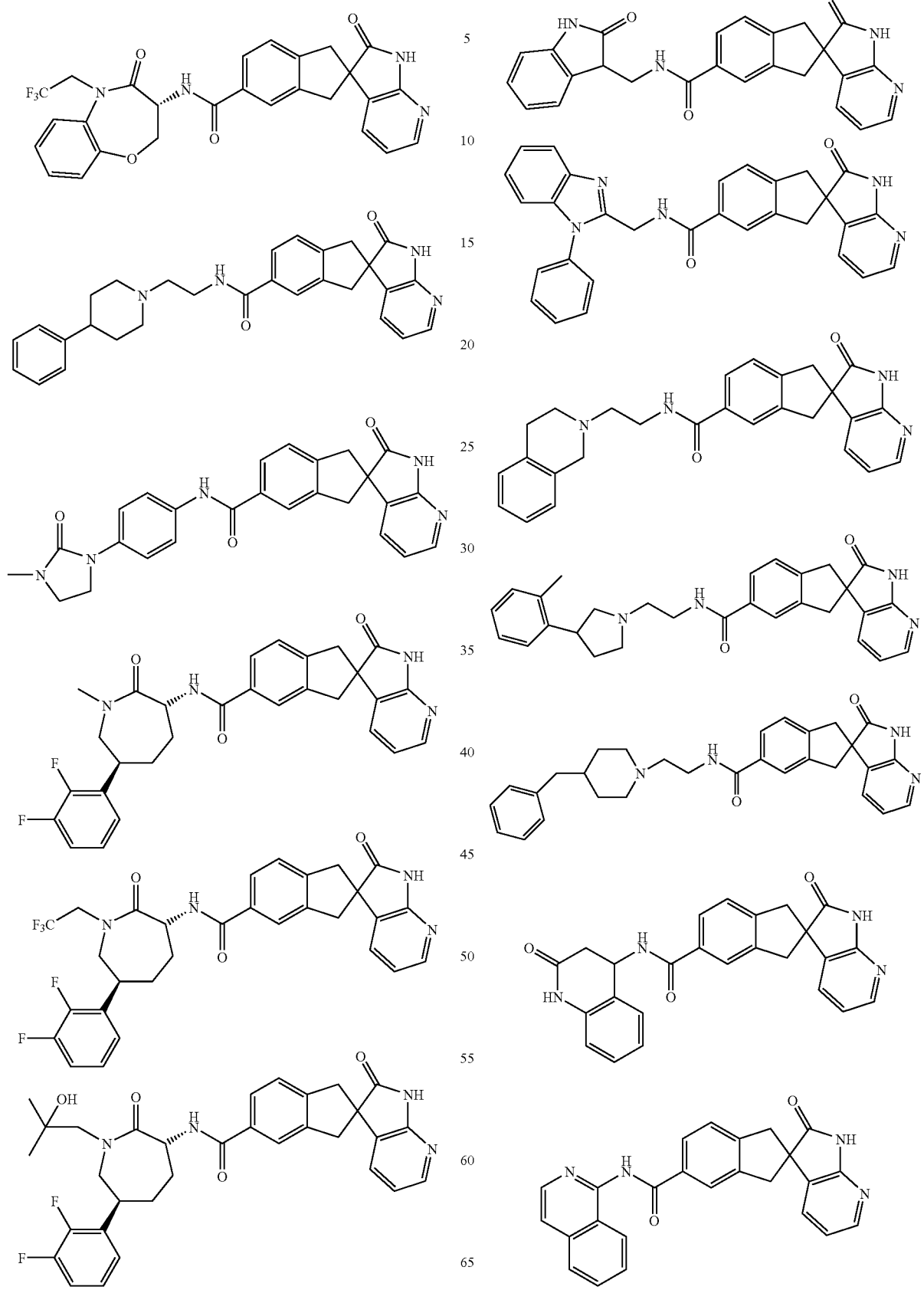

-continued
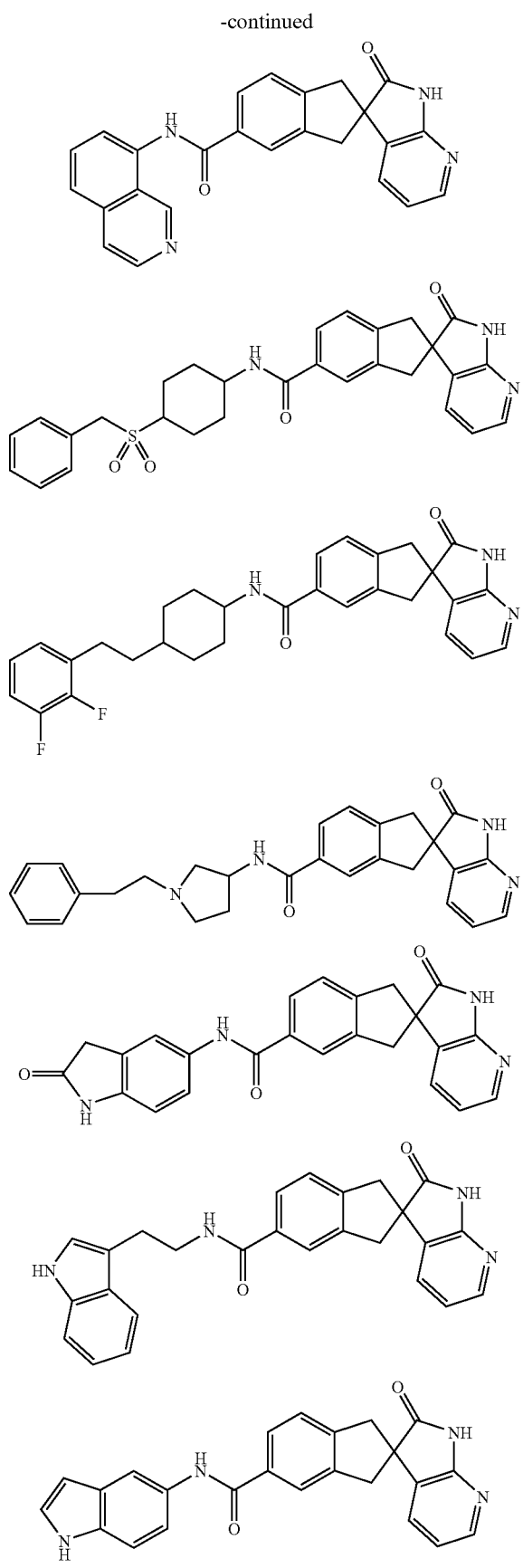
-continued
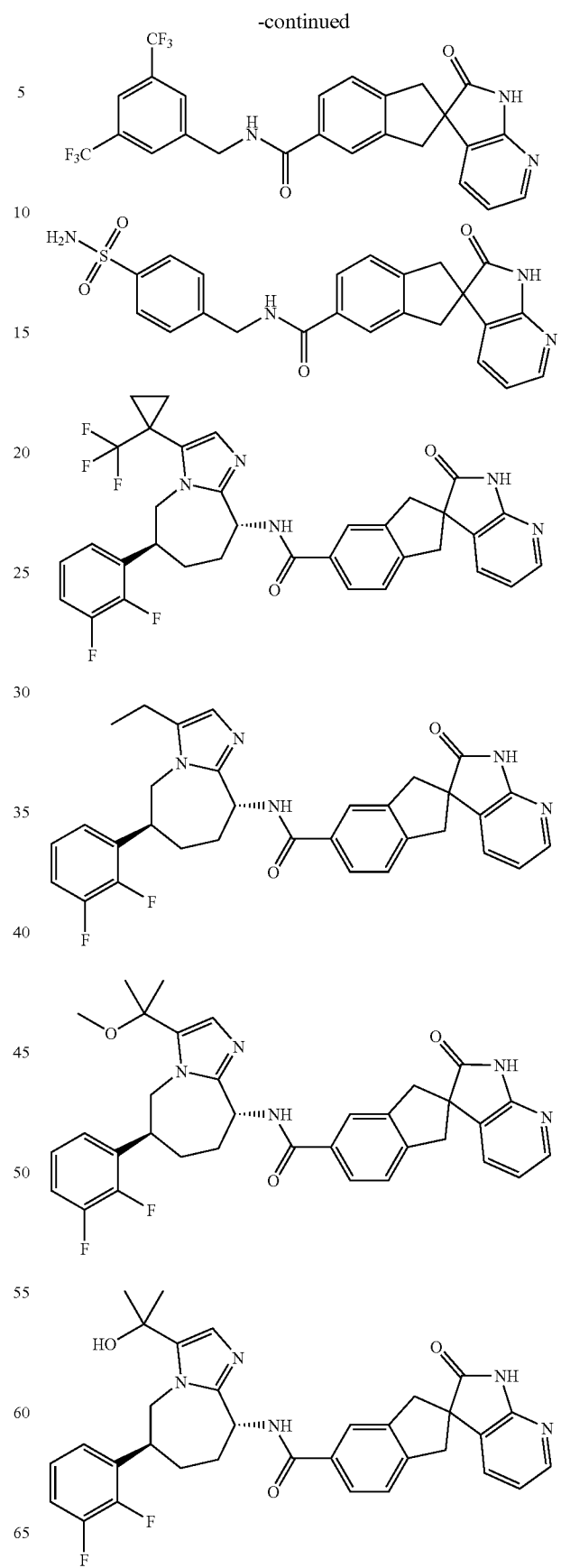

75
-continued
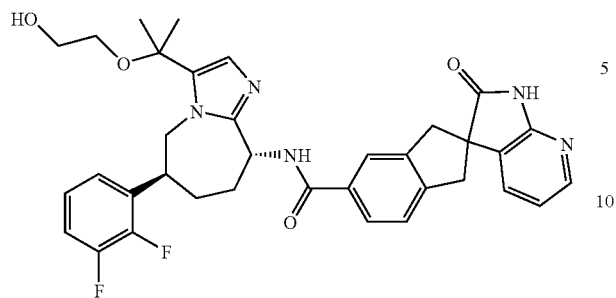
76
-continued
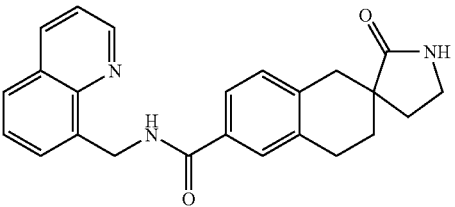
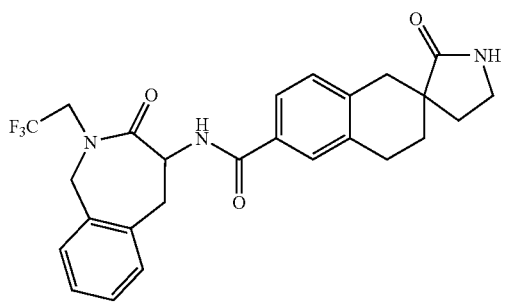
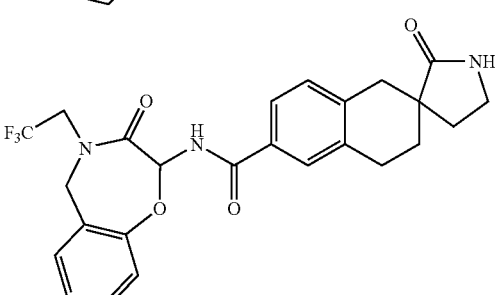
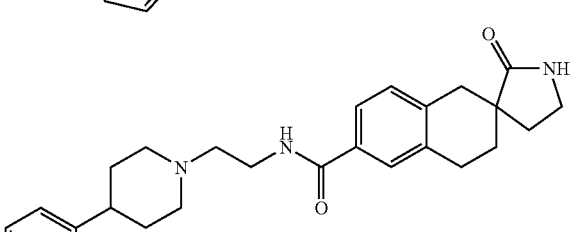
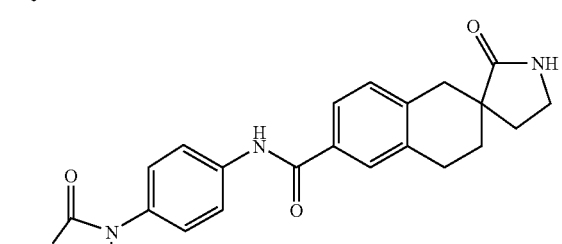
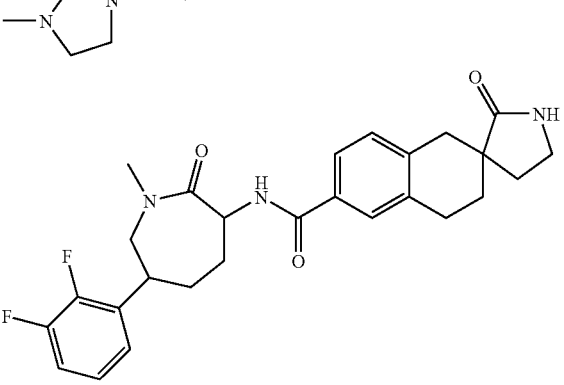

77 78
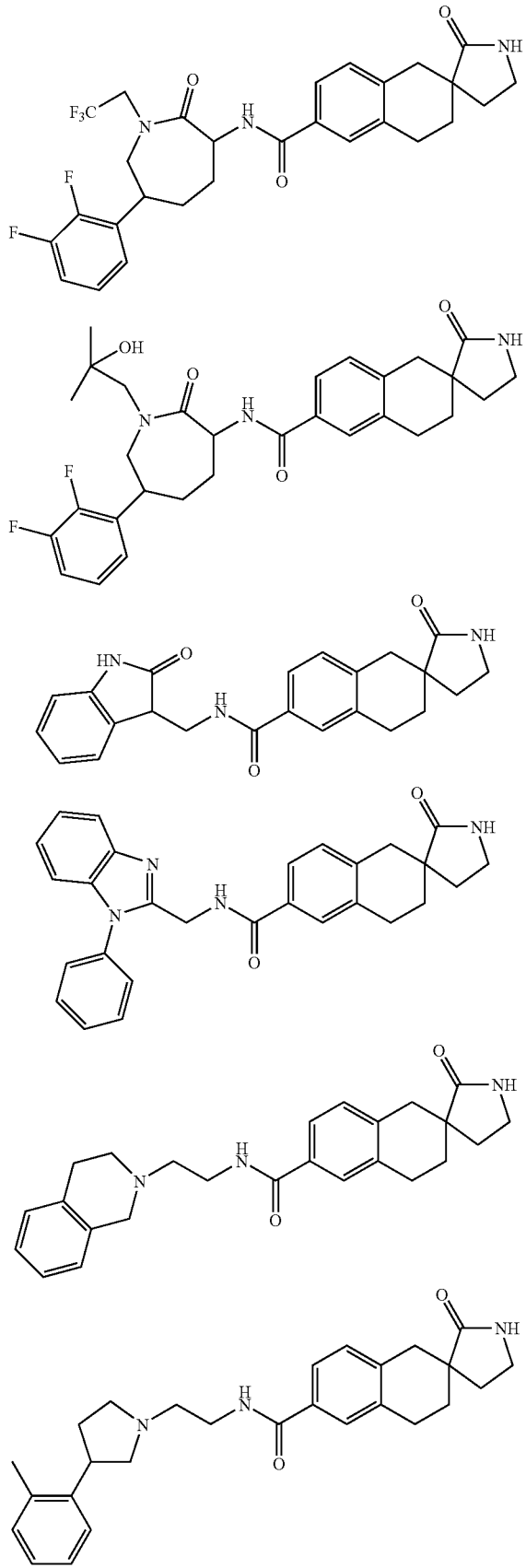
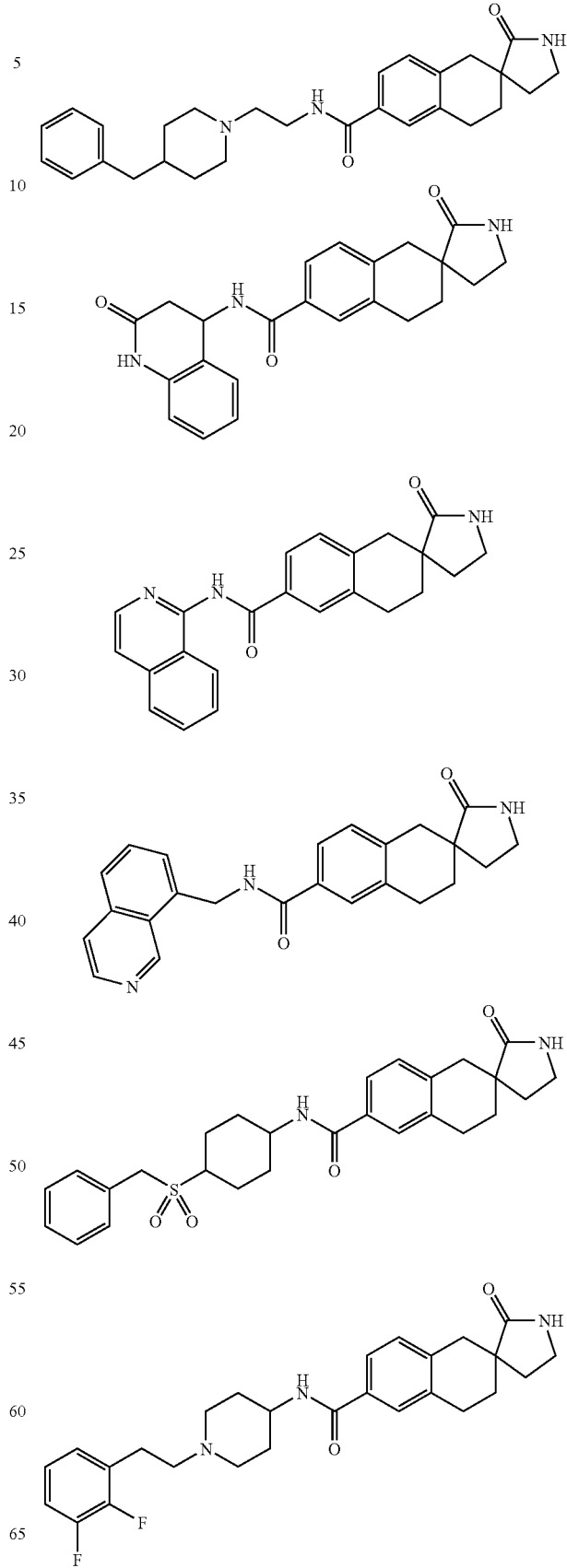

-continued

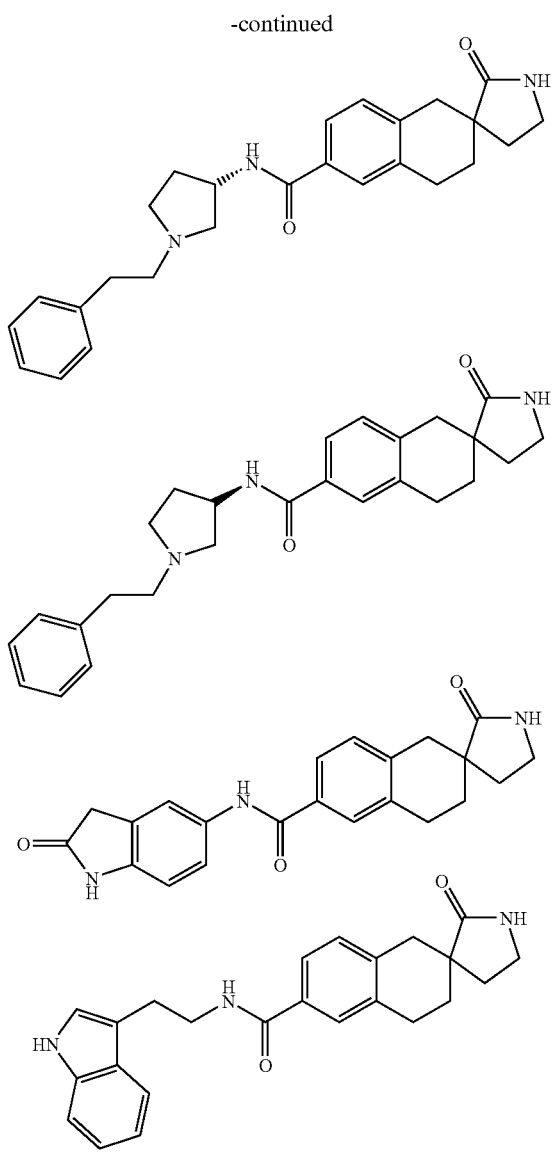

-continued

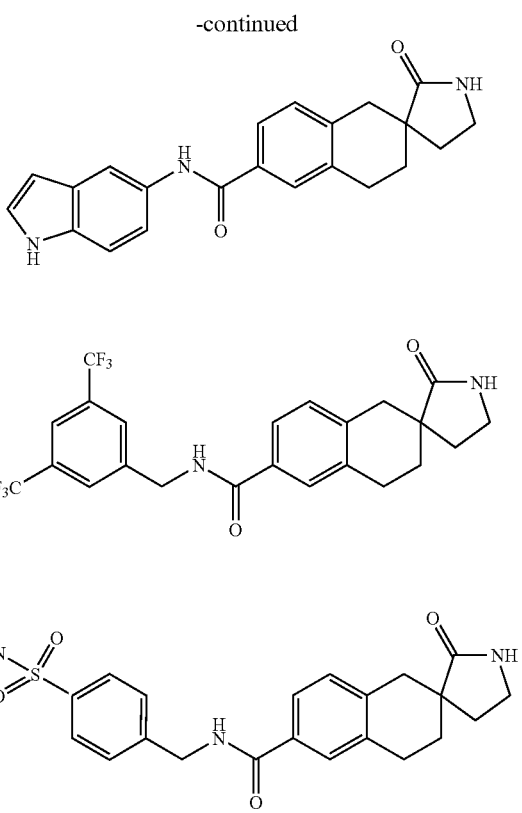

a pharmaceutically acceptable salt or individual diastereoisomer thereof.

22. A pharmaceutical composition which comprises an inert carrier and the compound of claim 1.

23. A method for treating, headache, migraine or cluster headache in a mammalian patient in need of such which comprises administering to the patient a therapeutically effective amount of the compound of claim 1.

* * * * *

UNITED STATES PATENT AND TRADEMARK OFFICE
CERTIFICATE OF CORRECTION

| | |
|---|---|
| PATENT NO. | : 7,390,798 B2 |
| APPLICATION NO. | : 11/660798 |
| DATED | : June 24, 2008 |
| INVENTOR(S) | : Theresa M. Williams et al. |

Page 1 of 1

It is certified that error appears in the above-identified patent and that said Letters Patent is hereby corrected as shown below:

On the cover page, item (22), delete "Feb. 9, 2005" and replace with -- Sept. 9, 2005 --.

Signed and Sealed this

Sixteenth Day of September, 2008

JON W. DUDAS
*Director of the United States Patent and Trademark Office*